(12) United States Patent
Glaesner et al.

(10) Patent No.: US 7,084,243 B2
(45) Date of Patent: Aug. 1, 2006

(54) GLUCAGON-LIKE PEPTIDE-1 ANALOGS

(75) Inventors: Wolfgang Glaesner, Indianapolis, IN (US); Rohn Lee Millican, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 158 days.

(21) Appl. No.: 10/276,772

(22) PCT Filed: Jun. 1, 2001

(86) PCT No.: PCT/US01/16474

§ 371 (c)(1),
(2), (4) Date: Nov. 19, 2002

(87) PCT Pub. No.: WO01/98331

PCT Pub. Date: Dec. 27, 2001

(65) Prior Publication Data

US 2003/0220243 A1    Nov. 27, 2003

Related U.S. Application Data

(60) Provisional application No. 60/240,349, filed on Oct. 13, 2000, provisional application No. 60/212,171, filed on Jun. 16, 2000.

(51) Int. Cl.
A61K 38/26 (2006.01)
A61K 38/00 (2006.01)
C12Q 1/00 (2006.01)
G01N 33/53 (2006.01)

(52) U.S. Cl. .................. 530/300; 530/308; 514/2; 435/4; 435/7.1

(58) Field of Classification Search ............... 530/300, 530/308; 514/12; 435/4, 7.1
See application file for complete search history.

(56) References Cited

U.S. PATENT DOCUMENTS

| 5,424,286 A | 6/1995 | Eng |
| 5,545,618 A | 8/1996 | Buckley et al. |
| 5,977,071 A | 11/1999 | Galloway et al. |

FOREIGN PATENT DOCUMENTS

| WO | WO 91 11457 | 8/1991 |
| WO | WO 98 19698 | 5/1998 |
| WO | WO 99/07404 | 2/1999 |
| WO | WO 99/25727 | 5/1999 |
| WO | WO 99/25728 | 5/1999 |
| WO | WO 99 30731 | 6/1999 |
| WO | WO 99/43341 | 9/1999 |
| WO | WO 99/43706 | 9/1999 |
| WO | WO 00 07617 | 2/2000 |

OTHER PUBLICATIONS

Aderlhorst et.al. J. Biol. Chem. 269:6275-6278, 1994.*
Deacon, CF et al, : "Dipeptidyl Peptidase IV Resistant Analogues of Glucagon—Like Peptide-1 Which Have Extended Metabolic Stability and Improved Biological Activity," Diabetologia, vol. 41, pp. 271-278, 1998 XP002202152 p. 276; figure 3; tables 1, 3.

* cited by examiner

Primary Examiner—Janet L. Andres
Assistant Examiner—Gyan Chandra
(74) Attorney, Agent, or Firm—Gregory A. Cox

(57) ABSTRACT

Disclosed are glucagon-like peptide-1 (GLP-1) compounds with modifications at one or more of the following positions: 11, 12, 16, 22, 23, 24, 25, 27, 30, 33, 34, 35, 36, or 37. Methods of treating these GLP-1 compounds are also disclosed.

14 Claims, 4 Drawing Sheets

```
His-Val-Glu-Gly-Thr-Phe-Thr-Ser-Asp-Val-Ser-Ser-Tyr-
Leu-Glu-Glu-Gln-Ala-Ala-Lys-Glu-Phe-Ile-Ala-Trp-Leu-
Val-Lys-Gly-Arg-Gly
```
$Val^8$-$Glu^{22}$-GLP-1(7-37)OH

```
His-Val-Glu-Gly-Thr-Phe-Thr-Ser-Asp-Val-Ser-Ser-Tyr-
Leu-Glu-Asp-Gln-Ala-Ala-Lys-Glu-Phe-Ile-Ala-Trp-Leu-
Val-Lys-Gly-Arg-Gly
```
$Val^8$-$Asp^{22}$-GLP-1(7-37)OH

```
His-Val-Glu-Gly-Thr-Phe-Thr-Ser-Asp-Val-Ser-Ser-Tyr-
Leu-Glu-Arg-Gln-Ala-Ala-Lys-Glu-Phe-Ile-Ala-Trp-Leu-
Val-Lys-Gly-Arg-Gly
```
$Val^8$-$Arg^{22}$-GLP-1(7-37)OH

```
His-Val-Glu-Gly-Thr-Phe-Thr-Ser-Asp-Val-Ser-Ser-Tyr-
Leu-Glu-Lys-Gln-Ala-Ala-Lys-Glu-Phe-Ile-Ala-Trp-Leu-
Val-Lys-Gly-Arg-Gly
```
$Val^8$-$Lys^{22}$-GLP-1(7-37)OH

Fig. 1

His-Val-Glu-Gly-Thr-Phe-Thr-Ser-Asp-Val-Ser-Ser-Tyr-
Leu-Glu-Glu-Gln-Ala-Ala-Lys-Glu-Phe-Ile-Ala-Trp-Leu-
Val-Lys-Gly-Arg-Gly $\qquad$ Val$^8$-Glu$^{22}$-GLP-1(7-37)OH His-Val-Glu-Gly-Thr-Phe-Thr-Ser-Asp-Val-Ser-Ser-Tyr-
Leu-Glu-Asp-Gln-Ala-Ala-Lys-Glu-Phe-Ile-Ala-Trp-Leu-
Val-Lys-Gly-Arg-Gly $\qquad$ Val$^8$-Asp$^{22}$-GLP-1(7-37)OH His-Val-Glu-Gly-Thr-Phe-Thr-Ser-Asp-Val-Ser-Ser-Tyr-
Leu-Glu-Arg-Gln-Ala-Ala-Lys-Glu-Phe-Ile-Ala-Trp-Leu-
Val-Lys-Gly-Arg-Gly $\qquad$ Val$^8$-Arg$^{22}$-GLP-1(7-37)OH His-Val-Glu-Gly-Thr-Phe-Thr-Ser-Asp-Val-Ser-Ser-Tyr-
Leu-Glu-Lys-Gln-Ala-Ala-Lys-Glu-Phe-Ile-Ala-Trp-Leu-
Val-Lys-Gly-Arg-Gly $\qquad$ Val$^8$-Lys$^{22}$-GLP-1(7-37)OH

Fig. 2

His-Gly-Glu-Gly-Thr-Phe-Thr-Ser-Asp-Val-Ser-Ser-Tyr-
Leu-Glu-Glu-Gln-Ala-Ala-Lys-Glu-Phe-Ile-Ala-Trp-Leu-
Val-Lys-Gly-Arg-Gly $Gly^8$-$Glu^{22}$-GLP-1(7-37)OH

His-Gly-Glu-Gly-Thr-Phe-Thr-Ser-Asp-Val-Ser-Ser-Tyr-
Leu-Glu-Asp-Gln-Ala-Ala-Lys-Glu-Phe-Ile-Ala-Trp-Leu-
Val-Lys-Gly-Arg-Gly $Gly^8$-$Asp^{22}$-GLP-1(7-37)OH

His-Gly-Glu-Gly-Thr-Phe-Thr-Ser-Asp-Val-Ser-Ser-Tyr-
Leu-Glu-Arg-Gln-Ala-Ala-Lys-Glu-Phe-Ile-Ala-Trp-Leu-
Val-Lys-Gly-Arg-Gly $Gly^8$-$Arg^{22}$-GLP-1(7-37)OH

His-Gly-Glu-Gly-Thr-Phe-Thr-Ser-Asp-Val-Ser-Ser-Tyr-
Leu-Glu-Lys-Gln-Ala-Ala-Lys-Glu-Phe-Ile-Ala-Trp-Leu-
Val-Lys-Gly-Arg-Gly $Gly^8$-$Lys^{22}$-GLP-1(7-37)OH

Fig. 3

His-Val-Glu-Gly-Thr-Phe-Thr-Ser-Asp-Val-Ser-Ser-Tyr-
Leu-Glu-Gly-Gln-Ala-Ala-Lys-Glu-Phe-Ile-Glu-Trp-Leu-
Val-Lys-Gly-Arg-Gly $\qquad$ Val$^8$-Glu$^{30}$-GLP-1(7-37)OH His-Gly-Glu-Gly-Thr-Phe-Thr-Ser-Asp-Val-Ser-Ser-Tyr-
Leu-Glu-Gly-Gln-Ala-Ala-Lys-Glu-Phe-Ile-Glu-Trp-Leu-
Val-Lys-Gly-Arg-Gly $\qquad$ Gly$^8$-Glu$^{30}$-GLP-1(7-37)OH His-Val-Glu-Gly-Thr-Phe-Thr-Ser-Asp-Val-Ser-Ser-Tyr-
Leu-Glu-Gly-Gln-Ala-Ala-Lys-Glu-Phe-Ile-Ala-Trp-Leu-
Val-Lys-Gly-Arg-His $\qquad$ Val$^8$-His$^{37}$-GLP-1(7-37)OH His-Gly-Glu-Gly-Thr-Phe-Thr-Ser-Asp-Val-Ser-Ser-Tyr-
Leu-Glu-Gly-Gln-Ala-Ala-Lys-Glu-Phe-Ile-Ala-Trp-Leu-
Val-Lys-Gly-Arg-His $\qquad$ Gly$^8$-His$^{37}$-GLP-1(7-37)OH

Fig. 4

His-Val-Glu-Gly-Thr-Phe-Thr-Ser-Asp-Val-Ser-Ser-Tyr-
Leu-Glu-Glu-Gln-Ala-Ala-Lys-Ala-Phe-Ile-Ala-Trp-Leu-
Val-Lys-Gly-Arg-His $\quad$ $Val^8$-$Glu^{22}$-$Ala^{27}$-GLP-1(7-37)OH His-Val-Glu-Gly-Thr-Phe-Thr-Ser-Asp-Val-Ser-Ser-Tyr-
Leu-Glu-Lys-Glu-Ala-Ala-Lys-Glu-Phe-Ile-Ala-Trp-Leu-
Val-Lys-Gly-Arg-His $\quad$ $Val^8$-$Lys^{22}$-$Glu^{23}$-GLP-1(7-37)OH

SEQUENCE LISTING

```
<160> NUMBER OF SEQ ID NOS: 53

<210> SEQ ID NO 1
<211> LENGTH: 31
<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (2)..(2)
<223> OTHER INFORMATION: Xaa at position 2 is Gly, Ala, Val, Leu, Ile,
      Ser, or Thr;
<220> FEATURE:
<221> NAME/KEY: VARIANT
<222> LOCATION: (5)..(5)
<223> OTHER INFORMATION: Xaa at position 5 is Asp, Glu, Arg, Thr, Ala,
      Lys, or His;
<220> FEATURE:
<221> NAME/KEY: VARIANT
<222> LOCATION: (6)..(6)
<223> OTHER INFORMATION: Xaa at position 6 is His, Trp, Phe, or Tyr;
<220> FEATURE:
<221> NAME/KEY: VARIANT
<222> LOCATION: (10)..(10)
<223> OTHER INFORMATION: Xaa at position 10 is Leu, Ser, Thr, Trp, His,
      Phe, Asp, Val, Glu , or Ala
<220> FEATURE:
<221> NAME/KEY: VARIANT
<222> LOCATION: (16)..(16)
<223> OTHER INFORMATION: Xaa at position 16 is Gly, Asp, Glu, Gln, Asn,
      Lys, Arg, or Cys;
<220> FEATURE:
<221> NAME/KEY: VARIANT
<222> LOCATION: (17)..(17)
```

-continued

```
<223> OTHER INFORMATION: Xaa at position 17 is His, Asp, Lys, Glu, or
      Gln;
<220> FEATURE:
<221> NAME/KEY: VARIANT
<222> LOCATION: (18)..(18)
<223> OTHER INFORMATION: Xaa at position 18 is Glu, His, Ala, or Lys;
<220> FEATURE:
<221> NAME/KEY: VARIANT
<222> LOCATION: (20)..(20)
<223> OTHER INFORMATION: Xaa at position 20 is Asp, Lys, Glu, or His;
<220> FEATURE:
<221> NAME/KEY: VARIANT
<222> LOCATION: (21)..(21)
<223> OTHER INFORMATION: Xaa at position 21 is Ala, Glu, His, Phe, Tyr,
      Trp, Arg, or Lys;
<220> FEATURE:
<221> NAME/KEY: VARIANT
<222> LOCATION: (25)..(25)
<223> OTHER INFORMATION: Xaa at position 25 is Ala, Glu, Asp, Ser, or
      His;
<220> FEATURE:
<221> NAME/KEY: VARIANT
<222> LOCATION: (27)..(27)
<223> OTHER INFORMATION: Xaa at position 27 is Asp, Arg, Val, Lys, Ala,
      Gly, or Glu;
<220> FEATURE:
<221> NAME/KEY: VARIANT
<222> LOCATION: (28)..(28)
<223> OTHER INFORMATION: Xaa at position 28 is Glu, Lys, or Asp;
<220> FEATURE:
<221> NAME/KEY: VARIANT
<222> LOCATION: (29)..(29)
<223> OTHER INFORMATION: Xaa at position 29 is Thr, Ser, Lys, Arg, Trp,
      Tyr, Phe, Asp, Gly, Pro, His, or Glu
<220> FEATURE:
<221> NAME/KEY: VARIANT
<222> LOCATION: (30)..(30)
<223> OTHER INFORMATION: Xaa at position 30 is Arg, Glu, or His;
<220> FEATURE:
<221> NAME/KEY: VARIANT
<222> LOCATION: (31)..(31)
<223> OTHER INFORMATION: Xaa at position 31 is Lys, Arg, Thr, Ser, Glu,
      Asp, Trp, Tyr, Phe, His, -NH2, Gly, Gly-Pro, or Gly-Pro-NH2, or is
      deleted

<400> SEQUENCE: 1

His Xaa Glu Gly Xaa Xaa Thr Ser Asp Xaa Ser Ser Tyr Leu Glu Xaa
1               5                   10                  15

Xaa Xaa Ala Xaa Xaa Phe Ile Ala Xaa Leu Xaa Xaa Xaa Xaa Xaa
            20                  25                  30

<210> SEQ ID NO 2
<211> LENGTH: 31
<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (2)..(2)
<223> OTHER INFORMATION: Xaa at postion 2 is Gly, Ala, Val, Leu, Ile,
      Ser, or Thr;
<220> FEATURE:
<221> NAME/KEY: VARIANT
<222> LOCATION: (6)..(6)
<223> OTHER INFORMATION: Xaa at postion 6 is His, Trp, Phe, or Tyr;
<220> FEATURE:
<221> NAME/KEY: VARIANT
<222> LOCATION: (10)..(10)
<223> OTHER INFORMATION: Xaa at postion 10 is Leu, Ser, Thr, Trp, His,
      Phe, Asp, Val, Glu, or Ala
<220> FEATURE:
<221> NAME/KEY: VARIANT
<222> LOCATION: (16)..(16)
<223> OTHER INFORMATION: Xaa at postion 16 is Gly, Asp, Glu, Gln, Asn,
      Lys, Arg, or Cys;
```

```
<220> FEATURE:
<221> NAME/KEY: VARIANT
<222> LOCATION: (17)..(17)
<223> OTHER INFORMATION: Xaa at postion 17 is His, Asp, Lys, Glu, or
      Gln;
<220> FEATURE:
<221> NAME/KEY: VARIANT
<222> LOCATION: (20)..(20)
<223> OTHER INFORMATION: Xaa at postion 20 is Asp, Lys, Glu, or His;
<220> FEATURE:
<221> NAME/KEY: VARIANT
<222> LOCATION: (24)..(24)
<223> OTHER INFORMATION: Xaa at postion 24 is Ala, Glu, Asp, Ser, or
      His;
<220> FEATURE:
<221> NAME/KEY: VARIANT
<222> LOCATION: (29)..(29)
<223> OTHER INFORMATION: Xaa at postion 29 is Thr, Ser, Lys, Arg, Trp,
      Tyr, Phe, Asp, Gly, Pro, His, or Glu
<220> FEATURE:
<221> NAME/KEY: VARIANT
<222> LOCATION: (31)..(31)
<223> OTHER INFORMATION: Xaa at postion 31 is Lys, Arg, Thr, Ser, Glu,
      Asp, Trp, Tyr, Phe, His, -NH2, Gly, Gly-Pro, or Gly-Pro-NH2, or is
      deleted

<400> SEQUENCE: 2

His Xaa Glu Gly Thr Xaa Thr Ser Asp Xaa Ser Ser Tyr Leu Glu Xaa
1               5                   10                  15

Xaa Ala Ala Xaa Glu Phe Ile Xaa Trp Leu Val Lys Xaa Arg Xaa
            20                  25                  30

<210> SEQ ID NO 3
<211> LENGTH: 31
<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (2)..(2)
<223> OTHER INFORMATION: Xaa at position 2 is Gly, Ala, Val, Leu, Ile,
      Ser, or Thr;
<220> FEATURE:
<221> NAME/KEY: VARIANT
<222> LOCATION: (16)..(16)
<223> OTHER INFORMATION: Xaa at position 16 is Gly, Asp, Glu, Gln, Asn,
      Lys, Arg, or Cys;
<220> FEATURE:
<221> NAME/KEY: VARIANT
<222> LOCATION: (17)..(17)
<223> OTHER INFORMATION: Xaa at position 17 is His, Asp, Lys, Glu, or
      Gln;
<220> FEATURE:
<221> NAME/KEY: VARIANT
<222> LOCATION: (21)..(21)
<223> OTHER INFORMATION: Xaa at position 21 is Ala, Glu, His, Phe, Tyr,
      Trp, Arg, or Lys;
<220> FEATURE:
<221> NAME/KEY: VARIANT
<222> LOCATION: (24)..(24)
<223> OTHER INFORMATION: Xaa at position 24 is Ala, Glu, Asp, Ser, or
      His;
<220> FEATURE:
<221> NAME/KEY: VARIANT
<222> LOCATION: (31)..(31)
<223> OTHER INFORMATION: Xaa at position 31 is Lys, Arg, Thr, Ser, Glu,
      Asp, Trp, Tyr, Phe, His, -NH2, Gly, Gly-Pro, or Gly-Pro-NH2, or is
      deleted

<400> SEQUENCE: 3

His Xaa Glu Gly Thr Phe Thr Ser Asp Val Ser Ser Tyr Leu Glu Xaa
1               5                   10                  15

Xaa Ala Ala Lys Xaa Phe Ile Xaa Trp Leu Val Lys Gly Arg Xaa
```

-continued

```
                  20                  25                  30

<210> SEQ ID NO 4
<211> LENGTH: 31
<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (1)..(1)
<223> OTHER INFORMATION: Xaa at position 1 is L-histidine, D-histidine,
      desamino-histidine, 2amino-histidine, Beta-hydroxy-histidine,
      homohistidine, alpha-fluoromethyl-histidine or alpha-methyl
      -histidine
<220> FEATURE:
<221> NAME/KEY: VARIANT
<222> LOCATION: (2)..(2)
<223> OTHER INFORMATION: Xaa at position 2 is Gly, Ala, Val, Leu, Ile,
      Ser, or Thr;
<220> FEATURE:
<221> NAME/KEY: VARIANT
<222> LOCATION: (16)..(16)
<223> OTHER INFORMATION: Xaa at position 16 is Asp, Glu, Gln, Asp, Lys,
      Arg, or Cys;
<220> FEATURE:
<221> NAME/KEY: VARIANT
<222> LOCATION: (31)..(31)
<223> OTHER INFORMATION: Xaa at position 31 is -NH2 or Gly.

<400> SEQUENCE: 4

Xaa Xaa Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Arg Xaa
            20                  25                  30

<210> SEQ ID NO 5
<211> LENGTH: 31
<212> TYPE: PRT
<213> ORGANISM: Artificial
<220> FEATURE:
<223> OTHER INFORMATION: synthetic construct

<400> SEQUENCE: 5

His Val Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly
            20                  25                  30

<210> SEQ ID NO 6
<211> LENGTH: 31
<212> TYPE: PRT
<213> ORGANISM: Artificial
<220> FEATURE:
<223> OTHER INFORMATION: synthetic construct

<400> SEQUENCE: 6

His Val Glu Gly Thr Phe Thr Ser Asp Val Ser Ser Tyr Leu Glu Asp
1               5                   10                  15

Gln Ala Ala Lys Glu Phe Ile Ala Trp Leu Val Lys Gly Arg Gly
            20                  25                  30

<210> SEQ ID NO 7
<211> LENGTH: 31
<212> TYPE: PRT
<213> ORGANISM: Artificial
<220> FEATURE:
<223> OTHER INFORMATION: synthetic construct
```

-continued

<400> SEQUENCE: 7

His Val Glu Gly Thr Phe Thr Ser Asp Val Ser Ser Tyr Leu Glu Arg
1               5                   10                  15

Gln Ala Ala Lys Glu Phe Ile Ala Trp Leu Val Lys Gly Arg Gly
            20                  25                  30

<210> SEQ ID NO 8
<211> LENGTH: 31
<212> TYPE: PRT
<213> ORGANISM: Artificial
<220> FEATURE:
<223> OTHER INFORMATION: synthetic construct

<400> SEQUENCE: 8

His Val Glu Gly Thr Phe Thr Ser Asp Val Ser Ser Tyr Leu Glu Lys
1               5                   10                  15

Gln Ala Ala Lys Glu Phe Ile Ala Trp Leu Val Lys Gly Arg Gly
            20                  25                  30

<210> SEQ ID NO 9
<211> LENGTH: 31
<212> TYPE: PRT
<213> ORGANISM: Artificial
<220> FEATURE:
<223> OTHER INFORMATION: synthetic construct

<400> SEQUENCE: 9

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly
            20                  25                  30

<210> SEQ ID NO 10
<211> LENGTH: 31
<212> TYPE: PRT
<213> ORGANISM: Artificial
<220> FEATURE:
<223> OTHER INFORMATION: synthetic construct

<400> SEQUENCE: 10

His Gly Glu Gly Thr Phe Thr Ser Asp Val Ser Ser Tyr Leu Glu Asp
1               5                   10                  15

Gln Ala Ala Lys Glu Phe Ile Ala Trp Leu Val Lys Gly Arg Gly
            20                  25                  30

<210> SEQ ID NO 11
<211> LENGTH: 31
<212> TYPE: PRT
<213> ORGANISM: Artificial
<220> FEATURE:
<223> OTHER INFORMATION: synthetic construct

<400> SEQUENCE: 11

His Gly Glu Gly Thr Phe Thr Ser Asp Val Ser Ser Tyr Leu Glu Arg
1               5                   10                  15

Gln Ala Ala Lys Glu Phe Ile Ala Trp Leu Val Lys Gly Arg Gly
            20                  25                  30

<210> SEQ ID NO 12
<211> LENGTH: 31
<212> TYPE: PRT
<213> ORGANISM: Artificial
<220> FEATURE:
<223> OTHER INFORMATION: synthetic construct

<400> SEQUENCE: 12

His Gly Glu Gly Thr Phe Thr Ser Asp Val Ser Ser Tyr Leu Glu Lys
1               5                   10                  15

Gln Ala Ala Lys Glu Phe Ile Ala Trp Leu Val Lys Gly Arg Gly
            20                  25                  30

<210> SEQ ID NO 13
<211> LENGTH: 31
<212> TYPE: PRT
<213> ORGANISM: Artificial
<220> FEATURE:
<223> OTHER INFORMATION: synthetic construct

<400> SEQUENCE: 13

His Val Glu Gly Thr Phe Thr Ser Asp Val Ser Ser Tyr Leu Glu Gly
1               5                   10                  15

Gln Ala Ala Lys Glu Phe Ile Glu Trp Leu Val Lys Gly Arg Gly
            20                  25                  30

<210> SEQ ID NO 14
<211> LENGTH: 31
<212> TYPE: PRT
<213> ORGANISM: Artificial
<220> FEATURE:
<223> OTHER INFORMATION: synthetic construct

<400> SEQUENCE: 14

His Gly Glu Gly Thr Phe Thr Ser Asp Val Ser Ser Tyr Leu Glu Gly
1               5                   10                  15

Gln Ala Ala Lys Glu Phe Ile Glu Trp Leu Val Lys Gly Arg Gly
            20                  25                  30

<210> SEQ ID NO 15
<211> LENGTH: 31
<212> TYPE: PRT
<213> ORGANISM: Artificial
<220> FEATURE:
<223> OTHER INFORMATION: synthetic construct

<400> SEQUENCE: 15

His Val Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg His
            20                  25                  30

<210> SEQ ID NO 16
<211> LENGTH: 31
<212> TYPE: PRT
<213> ORGANISM: Artificial
<220> FEATURE:
<223> OTHER INFORMATION: synthetic construct

<400> SEQUENCE: 16

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg His
            20                  25                  30

<210> SEQ ID NO 17
<211> LENGTH: 31
<212> TYPE: PRT
<213> ORGANISM: Artificial
<220> FEATURE:

<223> OTHER INFORMATION: synthetic construct

<400> SEQUENCE: 17

His Val Glu Gly Thr Phe Thr Ser Asp Val Ser Ser Tyr Leu Glu Glu
1               5                   10                  15
Gln Ala Ala Lys Ala Phe Ile Ala Trp Leu Val Lys Gly Arg His
            20                  25                  30

<210> SEQ ID NO 18
<211> LENGTH: 31
<212> TYPE: PRT
<213> ORGANISM: Artificial
<220> FEATURE:
<223> OTHER INFORMATION: synthetic construct

<400> SEQUENCE: 18

His Val Glu Gly Thr Phe Thr Ser Asp Val Ser Ser Tyr Leu Glu Lys
1               5                   10                  15
Glu Ala Ala Lys Glu Phe Ile Ala Trp Leu Val Lys Gly Arg His
            20                  25                  30

<210> SEQ ID NO 19
<211> LENGTH: 31
<212> TYPE: PRT
<213> ORGANISM: Homo sapiens

<400> SEQUENCE: 19

His Ala Glu Gly Thr Phe Thr Ser Asp Val Ser Ser Tyr Leu Glu Gly
1               5                   10                  15
Gln Ala Ala Lys Glu Phe Ile Ala Trp Leu Val Lys Gly Arg Gly
            20                  25                  30

<210> SEQ ID NO 20
<211> LENGTH: 31
<212> TYPE: PRT
<213> ORGANISM: Artificial
<220> FEATURE:
<223> OTHER INFORMATION: synthetic construct

<400> SEQUENCE: 20

His Ala Glu Gly Thr Phe Thr Ser Asp Val Ser Ser Tyr Leu Glu Glu
1               5                   10                  15
Gln Ala Ala Lys Glu Phe Ile Ala Trp Leu Val Lys Gly Arg Gly
            20                  25                  30

<210> SEQ ID NO 21
<211> LENGTH: 31
<212> TYPE: PRT
<213> ORGANISM: Artificial
<220> FEATURE:
<223> OTHER INFORMATION: synthetic construct

<400> SEQUENCE: 21

His Ala Glu Gly Thr Phe Thr Ser Asp Val Ser Ser Tyr Leu Glu Asp
1               5                   10                  15
Gln Ala Ala Lys Glu Phe Ile Ala Trp Leu Val Lys Gly Arg Gly
            20                  25                  30

<210> SEQ ID NO 22
<211> LENGTH: 31
<212> TYPE: PRT
<213> ORGANISM: Artificial
<220> FEATURE:
<223> OTHER INFORMATION: synthetic construct

<400> SEQUENCE: 22

His Ala Glu Gly Thr Phe Thr Ser Asp Val Ser Ser Tyr Leu Glu Arg
1               5                   10                  15

Gln Ala Ala Lys Glu Phe Ile Ala Trp Leu Val Lys Gly Arg Gly
            20                  25                  30

<210> SEQ ID NO 23
<211> LENGTH: 31
<212> TYPE: PRT
<213> ORGANISM: Artificial
<220> FEATURE:
<223> OTHER INFORMATION: synthetic construct

<400> SEQUENCE: 23

His Ala Glu Gly Thr Phe Thr Ser Asp Val Ser Ser Tyr Leu Glu Lys
1               5                   10                  15

Gln Ala Ala Lys Glu Phe Ile Ala Trp Leu Val Lys Gly Arg Gly
            20                  25                  30

<210> SEQ ID NO 24
<211> LENGTH: 31
<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (16)..(16)
<223> OTHER INFORMATION: Xaa at position 16 is cysteic acid.

<400> SEQUENCE: 24

His Ala Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Arg Gly
            20                  25                  30

<210> SEQ ID NO 25
<211> LENGTH: 31
<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (16)..(16)
<223> OTHER INFORMATION: Xaa at position 16 is cysteic acid.

<400> SEQUENCE: 25

His Val Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Arg Gly
            20                  25                  30

<210> SEQ ID NO 26
<211> LENGTH: 31
<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (16)..(16)
<223> OTHER INFORMATION: Xaa at position 16 is cysteic acid.

<400> SEQUENCE: 26

His Gly Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Arg Gly
            20                  25                  30

<210> SEQ ID NO 27
<211> LENGTH: 30
<212> TYPE: PRT
<213> ORGANISM: Artificial
<220> FEATURE:
<223> OTHER INFORMATION: synthetic construct

<400> SEQUENCE: 27

His Ala Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg
            20                  25                  30

<210> SEQ ID NO 28
<211> LENGTH: 30
<212> TYPE: PRT
<213> ORGANISM: Artificial
<220> FEATURE:
<223> OTHER INFORMATION: synthetic construct

<400> SEQUENCE: 28

His Ala Glu Gly Thr Phe Thr Ser Asp Val Ser Ser Tyr Leu Glu Asp
1               5                   10                  15

Gln Ala Ala Lys Glu Phe Ile Ala Trp Leu Val Lys Gly Arg
            20                  25                  30

<210> SEQ ID NO 29
<211> LENGTH: 30
<212> TYPE: PRT
<213> ORGANISM: Artificial
<220> FEATURE:
<223> OTHER INFORMATION: synthetic construct

<400> SEQUENCE: 29

His Ala Glu Gly Thr Phe Thr Ser Asp Val Ser Ser Tyr Leu Glu Arg
1               5                   10                  15

Gln Ala Ala Lys Glu Phe Ile Ala Trp Leu Val Lys Gly Arg
            20                  25                  30

<210> SEQ ID NO 30
<211> LENGTH: 30
<212> TYPE: PRT
<213> ORGANISM: Artificial
<220> FEATURE:
<223> OTHER INFORMATION: synthetic construct

<400> SEQUENCE: 30

His Ala Glu Gly Thr Phe Thr Ser Asp Val Ser Ser Tyr Leu Glu Lys
1               5                   10                  15

Gln Ala Ala Lys Glu Phe Ile Ala Trp Leu Val Lys Gly Arg
            20                  25                  30

<210> SEQ ID NO 31
<211> LENGTH: 30
<212> TYPE: PRT
<213> ORGANISM: Artificial
<220> FEATURE:
<223> OTHER INFORMATION: synthetic construct
<220> FEATURE:
<221> NAME/KEY: VARIANT

```
<222> LOCATION: (16)..(16)
<223> OTHER INFORMATION: Xaa at position 16 is cysteic acid.

<400> SEQUENCE: 31

His Ala Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Arg
            20                  25                  30

<210> SEQ ID NO 32
<211> LENGTH: 30
<212> TYPE: PRT
<213> ORGANISM: Artificial
<220> FEATURE:
<223> OTHER INFORMATION: synthetic construct

<400> SEQUENCE: 32

His Val Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg
            20                  25                  30

<210> SEQ ID NO 33
<211> LENGTH: 30
<212> TYPE: PRT
<213> ORGANISM: Artificial
<220> FEATURE:
<223> OTHER INFORMATION: synthetic construct

<400> SEQUENCE: 33

His Val Glu Gly Thr Phe Thr Ser Asp Val Ser Ser Tyr Leu Glu Asp
1               5                   10                  15

Gln Ala Ala Lys Glu Phe Ile Ala Trp Leu Val Lys Gly Arg
            20                  25                  30

<210> SEQ ID NO 34
<211> LENGTH: 30
<212> TYPE: PRT
<213> ORGANISM: Artificial
<220> FEATURE:
<223> OTHER INFORMATION: synthetic construct

<400> SEQUENCE: 34

His Val Glu Gly Thr Phe Thr Ser Asp Val Ser Ser Tyr Leu Glu Arg
1               5                   10                  15

Gln Ala Ala Lys Glu Phe Ile Ala Trp Leu Val Lys Gly Arg
            20                  25                  30

<210> SEQ ID NO 35
<211> LENGTH: 30
<212> TYPE: PRT
<213> ORGANISM: Artificial
<220> FEATURE:
<223> OTHER INFORMATION: synthetic construct

<400> SEQUENCE: 35

His Val Glu Gly Thr Phe Thr Ser Asp Val Ser Ser Tyr Leu Glu Lys
1               5                   10                  15

Gln Ala Ala Lys Glu Phe Ile Ala Trp Leu Val Lys Gly Arg
            20                  25                  30

<210> SEQ ID NO 36
<211> LENGTH: 30
<212> TYPE: PRT
```

-continued

```
<213> ORGANISM: Artificial
<220> FEATURE:
<223> OTHER INFORMATION: synthetic construct
<220> FEATURE:
<221> NAME/KEY: VARIANT
<222> LOCATION: (16)..(16)
<223> OTHER INFORMATION: Xaa at position 16 is cysteic acid.

<400> SEQUENCE: 36
```

His Val Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Arg
            20                  25                  30

```
<210> SEQ ID NO 37
<211> LENGTH: 30
<212> TYPE: PRT
<213> ORGANISM: Artificial
<220> FEATURE:
<223> OTHER INFORMATION: synthetic construct

<400> SEQUENCE: 37
```

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg
            20                  25                  30

```
<210> SEQ ID NO 38
<211> LENGTH: 30
<212> TYPE: PRT
<213> ORGANISM: Artificial
<220> FEATURE:
<223> OTHER INFORMATION: synthetic construct

<400> SEQUENCE: 38
```

His Gly Glu Gly Thr Phe Thr Ser Asp Val Ser Ser Tyr Leu Glu Asp
1               5                   10                  15

Gln Ala Ala Lys Glu Phe Ile Ala Trp Leu Val Lys Gly Arg
            20                  25                  30

```
<210> SEQ ID NO 39
<211> LENGTH: 30
<212> TYPE: PRT
<213> ORGANISM: Artificial
<220> FEATURE:
<223> OTHER INFORMATION: synthetic construct

<400> SEQUENCE: 39
```

His Gly Glu Gly Thr Phe Thr Ser Asp Val Ser Ser Tyr Leu Glu Arg
1               5                   10                  15

Gln Ala Ala Lys Glu Phe Ile Ala Trp Leu Val Lys Gly Arg
            20                  25                  30

```
<210> SEQ ID NO 40
<211> LENGTH: 30
<212> TYPE: PRT
<213> ORGANISM: Artificial
<220> FEATURE:
<223> OTHER INFORMATION: synthetic construct

<400> SEQUENCE: 40
```

His Gly Glu Gly Thr Phe Thr Ser Asp Val Ser Ser Tyr Leu Glu Lys
1               5                   10                  15

Gln Ala Ala Lys Glu Phe Ile Ala Trp Leu Val Lys Gly Arg
            20                  25                  30

<210> SEQ ID NO 41
<211> LENGTH: 30
<212> TYPE: PRT
<213> ORGANISM: Artificial
<220> FEATURE:
<223> OTHER INFORMATION: synthetic construct
<220> FEATURE:
<221> NAME/KEY: VARIANT
<222> LOCATION: (16)..(16)
<223> OTHER INFORMATION: Xaa at position 16 is cysteic acid.

<400> SEQUENCE: 41

His Gly Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Arg
            20                  25                  30

<210> SEQ ID NO 42
<211> LENGTH: 31
<212> TYPE: PRT
<213> ORGANISM: Artificial
<220> FEATURE:
<223> OTHER INFORMATION: synthetic construct

<400> SEQUENCE: 42

His Val Glu Gly Thr Phe Thr Ser Asp Val Ser Ser Tyr Leu Glu Gly
1               5                   10                  15

Lys Ala Ala Lys Glu Phe Ile Ala Trp Leu Val Lys Gly Arg Gly
            20                  25                  30

<210> SEQ ID NO 43
<211> LENGTH: 31
<212> TYPE: PRT
<213> ORGANISM: Artificial
<220> FEATURE:
<223> OTHER INFORMATION: synthetic construct

<400> SEQUENCE: 43

His Val Glu Gly Thr Phe Thr Ser Asp Val Ser Ser Tyr Leu Glu Gly
1               5                   10                  15

Gln Ala Ala Lys Ala Phe Ile Ala Trp Leu Val Lys Gly Arg Gly
            20                  25                  30

<210> SEQ ID NO 44
<211> LENGTH: 31
<212> TYPE: PRT
<213> ORGANISM: Artificial
<220> FEATURE:
<223> OTHER INFORMATION: synthetic construct

<400> SEQUENCE: 44

His Val Glu Gly Thr Phe Thr Ser Asp Val Ser Ser Tyr Leu Glu Gly
1               5                   10                  15

Gln Ala Ala Lys Glu Phe Ile Glu Trp Leu Val Lys Gly Arg Gly
            20                  25                  30

<210> SEQ ID NO 45
<211> LENGTH: 31
<212> TYPE: PRT
<213> ORGANISM: Artificial
<220> FEATURE:
<223> OTHER INFORMATION: synthetic construct

<400> SEQUENCE: 45

His Gly Glu Gly Thr Phe Thr Ser Asp Val Ser Ser Tyr Leu Glu Gly
1               5                   10                  15

Gln Ala Ala Lys Glu Phe Ile Glu Trp Leu Val Lys Gly Arg Gly
            20                  25                  30

<210> SEQ ID NO 46
<211> LENGTH: 31
<212> TYPE: PRT
<213> ORGANISM: Artificial
<220> FEATURE:
<223> OTHER INFORMATION: synthetic construct

<400> SEQUENCE: 46

His Val Glu Gly Thr Phe Thr Ser Asp Val Ser Ser Tyr Leu Glu Gly
1               5                   10                  15

Gln Ala Ala Lys Glu Phe Ile Ala Trp Leu Val Lys His Arg Gly
            20                  25                  30

<210> SEQ ID NO 47
<211> LENGTH: 31
<212> TYPE: PRT
<213> ORGANISM: Artificial
<220> FEATURE:
<223> OTHER INFORMATION: synthetic construct

<400> SEQUENCE: 47

His Val Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg His
            20                  25                  30

<210> SEQ ID NO 48
<211> LENGTH: 31
<212> TYPE: PRT
<213> ORGANISM: Artificial
<220> FEATURE:
<223> OTHER INFORMATION: synthetic construct

<400> SEQUENCE: 48

His Val Glu Gly Thr Phe Thr Ser Asp Val Ser Ser Tyr Leu Glu Glu
1               5                   10                  15

Lys Ala Ala Lys Glu Phe Ile Ala Trp Leu Val Lys Gly Arg Gly
            20                  25                  30

<210> SEQ ID NO 49
<211> LENGTH: 31
<212> TYPE: PRT
<213> ORGANISM: Artificial
<220> FEATURE:
<223> OTHER INFORMATION: synthetic construct

<400> SEQUENCE: 49

His Val Glu Gly Thr Phe Thr Ser Asp Val Ser Ser Tyr Leu Glu Glu
1               5                   10                  15

Glu Ala Ala Lys Glu Phe Ile Ala Trp Leu Val Lys Gly Arg Gly
            20                  25                  30

<210> SEQ ID NO 50
<211> LENGTH: 31
<212> TYPE: PRT
<213> ORGANISM: Artificial
<220> FEATURE:
<223> OTHER INFORMATION: synthetic construct

<400> SEQUENCE: 50

```
His Val Glu Gly Thr Phe Thr Ser Asp Val Ser Ser Tyr Leu Glu Glu
1               5                   10                  15

Gln Ala Ala Lys Ala Phe Ile Ala Trp Leu Val Lys Gly Arg Gly
            20                  25                  30
```

<210> SEQ ID NO 51
<211> LENGTH: 31
<212> TYPE: PRT
<213> ORGANISM: Artificial
<220> FEATURE:
<223> OTHER INFORMATION: synthetic construct

<400> SEQUENCE: 51

```
His Val Glu Gly Thr Phe Thr Ser Asp Val Ser Ser Tyr Leu Glu Gly
1               5                   10                  15

Gln Ala Ala Lys Glu Phe Ile Ala Trp Leu Val Gly Lys Arg Gly
            20                  25                  30
```

<210> SEQ ID NO 52
<211> LENGTH: 31
<212> TYPE: PRT
<213> ORGANISM: Artificial
<220> FEATURE:
<223> OTHER INFORMATION: synthetic construct

<400> SEQUENCE: 52

```
His Val Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg His
            20                  25                  30
```

<210> SEQ ID NO 53
<211> LENGTH: 31
<212> TYPE: PRT
<213> ORGANISM: Artificial
<220> FEATURE:
<223> OTHER INFORMATION: synthetic construct

<400> SEQUENCE: 53

```
His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg His
            20                  25                  30
```

GLUCAGON-LIKE PEPTIDE-1 ANALOGS

This is the national phase application, under 35 USC 371, for PCT/US01/16474, filed Jun. 1, 2001, which claims the priority of U.S. provisional application No. 60/212,171, filed Jun. 16, 2000, and U.S. provisional application No. 60/240,349, filed Oct. 13, 2000.

Glucagon-Like Peptide 1 (GLP-1) is a 37 amino acid peptide that is secreted by the L-cells of the intestine in response to food ingestion. It has been found to stimulate insulin secretion (insulinotropic action), thereby causing glucose uptake by cells and decreased serum glucose levels (see, e g., Mojsov, S., *Int. J. Peptide Protein Research*, 40:333–343 (1992)). However, GLP-1(1–37) is poorly active and attention has been focused on truncated analogs, referred to as GLP compounds, which are biologically much more potent than GLP-1. Examples. include GLP-1(7–37), GLP-1(7–36)NH$_2$, Gly$^8$-GLP-1(7–37)OH and Ser$^{34}$-GLP-1(7–37)OH. Because of their ability to stimulate insulin secretion, GLP compounds show great promise as agents for the treatment of diabetes, obesity, and related conditions.

GLP-1 compounds can exist in at least two different forms. The first form is physiologically active and dissolves readily in aqueous solution at physiological pH (7.4). In contrast, the second form has little or no insulinotropic activity and is substantially insoluble in water at pH 7.4. Unfortunately, the inactive form is readily produced when aqueous GLP-1 solutions are agitated, exposed to hydrophobic surfaces or have large air/water interfaces. The tendency to convert to the insoluble form considerably complicates the production of commercial quantities of active GLP-1 compounds; mixing operations or continuous movement through a pump are common operations in bulk manufacturing processes and these operations cause the agitation, air/water interfaces and/or contact with hydrophobic surfaces that results in the insoluble form. Conversion to the inactive form may also occur during storage or after administration to a patient, further complicating the use of these compounds as drugs. Therefore, there is a great need for biologically active GLP-1 analogs which convert less readily to the insoluble form than currently available GLP-1 compounds.

It has now been found that a number of GLP-1 analogs with modifications at one or more of the following positions: 11, 12, 16, 22, 23, 24, 26, 27, 30, 33, 34, 35, 36 or 37, show markedly decreased propensity to aggregate compared with GLP-1(7–37)OH.

Many of these analogs retain GLP-1 receptor activation that is comparable and in some cases greater than known GLP-1 compounds such as GLP-1(7–37)OH and Val$^8$-GLP-1(7–37)OH. For example, the aggregation time of Val$^8$-Glu$^{22}$-GLP(7–37)OH is over twenty fold greater and its GLP-1 receptor activation is about 25% greater than GLP-1(7–37)OH. Based on these discoveries, novel GLP-1 compounds and methods of treatment using the novel GLP-1 compounds are disclosed herein.

One embodiment of the present invention is a polypeptide having the amino acid sequence of formula I (SEQ ID NO: 1):

(SEQ ID NO: 1)
His-Xaa$_8$-Glu-Gly-Xaa$_{11}$-Xaa$_{12}$-Thr-Ser-Asp-Xaa$_{16}$-

Ser-Ser-Tyr-Leu-Glu-Xaa$_{22}$-Xaa$_{23}$-Xaa$_{24}$-Ala-Xaa$_{26}$-

-continued
Xaa$_{27}$-Phe-Ile-Ala-Xaa$_{31}$-Leu-Xaa$_{33}$-Xaa$_{34}$-Xaa$_{35}$-

Xaa$_{36}$-R formula I wherein:
Xaa$_8$ is: Gly, Ala, Val, Leu, Ile, Ser, or Thr;
Xaa$_{11}$ is: Asp, Glu, Arg, Thr, Ala, Lys, or His;
Xaa$_{12}$ is: His, Trp, Phe, or Tyr;
Xaa$_{16}$ is: Leu, Ser, Thr, Trp, His, Phe, Asp, Val, Tyr, Glu, or Ala;
Xaa$_{22}$ is: Gly, Asp, Glu, Gln, Asn, Lys, Arg, Cys, or Cysteic Acid;
Xaa$_{23}$ is: His, Asp, Lys, Glu, or Gln;
Xaa$_{24}$ is: Glu, His, Ala, or Lys;
Xaa$_{26}$ is: Asp, Lys, Glu, or His;
Xaa$_{27}$ is: Ala, Glu, His, Phe, Tyr, Trp, Arg, or Lys;
Xaa$_{30}$ is: Ala, Glu, Asp, Ser, or His;
Xaa$_{33}$ is: Asp, Arg, Val, Lys, Ala, Gly, or Glu;
Xaa$_{34}$ is: Glu, Lys, or Asp;
Xaa$_{35}$ is: Thr, Ser, Lys, Arg, Trp, Tyr, Phe, Asp, Gly, Pro, His, or Glu;
Xaa$_{36}$ is: Arg, Glu, or His;
R is: Lys, Arg, Thr, Ser, Glu, Asp, Trp, Tyr, Phe, His, —NH$_2$, Gly, Gly-Pro, or Gly-Pro-NH$_2$, or is deleted.

provided that the polypeptide does not have the sequence of GLP-1(7–37)OH or GLP-1(7–36)-NH$_2$ and provided that the polypeptide is not Gly$^8$-GLP-1(7–37)OH, Gly$^8$-GLP-1(7–36)NH$_2$, Val$^8$-GLP-1(7–37)OH, Val$^8$-GLP-1(7–36)NH$_2$, Leu8-GLP-1(7–37)OH, Leu$^8$-GLP-1(7–36)NH$_2$, Ile$^8$-GLP-1(7–37)OH, Ile$^8$-GLP-1(7–36)NH$_2$, Ser$^8$-GLP-1(7–37)OH, Ser$^8$-GLP-1(7–36)NH$_2$, Thr$^8$-GLP-1(7–37)OH, or Thr$^8$-GLP-1(7–36)NH$_2$, Ala$^{11}$-Glp-1(7–37)OH, Ala$^{11}$-Glp-1(7–36)NH$_2$, Ala$^{16}$-Glp-1(7–37)OH, Ala$^{16}$-Glp-1(7–36)NH$_2$, Ala$^{27}$-Glp-1(7–37)OH, Ala$^{27}$-Glp-1(7–36)NH$_2$, Ala$^{27}$-Glp-1(7–37)OH, Ala$^{27}$-Glp-1(7–36)NH$_2$, Ala$^{33}$-Glp-1(7–37)OH, or Ala$^{33}$-Glp-1(7–36)NH$_2$.

Another embodiment of the present invention is a polypeptide having the amino acid sequence of formula II (SEQ ID NO: 2):

(SEQ ID NO: 2)
His-Xaa$_8$-Glu-Gly-Thr-Xaa$_{12}$-Thr-Ser-Asp-Xaa$_{16}$-Ser-

Ser-Tyr-Leu-Glu-Xaa$_{22}$-Xaa$_{23}$-Ala-Ala-Xaa$_{26}$-Glu-Phe-

Ile-Xaa$_{30}$-Trp-Leu-Val-Lys-Xaa$_{35}$-Arg-R formula II wherein:
Xaa$_8$ is: Gly, Ala, Val, Leu, Ile, Ser, or Thr;
Xaa$_{12}$ is: His, Trp, Phe, or Tyr;
Xaa$_{16}$ is: Leu, Ser, Thr, Trp, His, Phe, Asp, Val, Glu, or Ala;
Xaa$_{22}$ is: Gly, Asp, Glu, Gln, Asn, Lys, Arg, Cys, or Cysteic Acid;
Xaa$_{23}$ is: His, Asp, Lys, Glu, or Gln;
Xaa$_{26}$ is: Asp, Lys, Glu, or His;
Xaa$_{30}$ is: Ala, Glu, Asp, Ser, or His;
Xaa$_{35}$ is: Thr, Ser, Lys, Arg, Trp, Tyr, Phe, Asp, Gly, Pro, His, or Glu;
R is: Lys, Arg, Thr, Ser, Glu, Asp, Trp, Tyr, Phe, His, —NH$_2$, Gly, Gly-Pro, or Gly-Pro-NH$_2$, or is deleted.

provided that the polypeptide does not have the sequence of GLP-1(7–37)OH or GLP-1(7–36)-NH$_2$ and provided that the polypeptide is not Gly$^8$-GLP-1(7–37)OH, Gly$^8$-GLP-1(7–36)NH$_2$, Val$^8$-GLP-1(7–37)OH, Val$^8$-GLP-1(7–36)NH$_2$, Leu$^8$-GLP-1(7–37)OH, Leu$^8$-GLP-1(7–36)NH$_2$, Ile$^8$-GLP- 1(7–37)OH, Ile⁸-GLP-1(7–36)NH₂, Ser⁸-GLP-1(7–37)OH, Ser⁸-GLP-1(7–36)NH₂, Thr⁸-GLP-1(7–37)OH, Thr⁸-GLP-1(7–36)NH₂, Ala¹⁶-GLP(7–37) OH, or Ala¹⁶-Glp-1 (7–36) NH₂.

Another embodiment of the present invention is a polypeptide having the amino acid sequence of formula III (SEQ ID NO: 3):

```
                                                    (SEQ ID NO: 3)
His-Xaa₈-Glu-Gly-Thr-Phe-Thr-Ser-Asp-Val-Ser-Ser-

Tyr-Leu-Glu-Xaa₂₂-Xaa₂₃-Ala-Ala-Lys-Xaa₂₇-Phe-Ile-

Xaa₃₀-Trp-Leu-Val-Lys-Gly-Arg-R formula III
``` wherein:
Xaa₈ is: Gly, Ala, Val, Leu, Ile, Ser, or Thr;
Xaa₂₂ is: Gly, Asp, Glu, Gln, Asn, Lys, Arg, Cys, or Cysteic Acid;
Xaa₂₃ is: His, Asp, Lys, Glu, or Gln;
Xaa₂₇ is: Ala, Glu, His, Phe, Tyr, Trp, Arg, or Lys
Xaa₃₀ is: Ala, Glu, Asp, Ser, or His;
R is: Lys, Arg, Thr, Ser, Glu, Asp, Trp, Tyr, Phe, His, —NH₂, Gly, Gly-Pro, or Gly-Pro-NH₂, or is deleted.
provided that the polypeptide does not have the sequence of GLP-1(7–37)OH or GLP-1(7–36)-NH₂ and provided that the polypeptide is not Gly⁸-GLP-1(7–37)OH, Gly⁸-GLP-1(7–36)NH₂, Val⁸-GLP-1(7–37)OH, Val⁸-GLP-1(7–36)NH₂, Leu⁸-GLP-1(7–37)OH, Leu⁸-GLP-1(7–36)NH₂, Ile⁸-GLP-1(7–37)OH, Ile⁸-GLP-1(7–36)NH₂, Ser⁸-GLP-1(7–37)OH, Ser⁸-GLP-1(7–36)NH₂, Thr⁸-GLP-1(7–37)OH, Thr⁸-GLP-1(7–36)NH₂, Ala¹⁶-Glp-1(7–37)OH, Ala¹⁶-Glp-1(7–36)NH₂, Glu²⁷-Glp-1(7–37)OH, or Glu²⁷-Glp-1(7–36)NH₂.

Another embodiment of the present invention is a polypeptide having the amino acid sequence of formula IV (SEQ ID NO: 4):

```
                                                    (SEQ ID NO: 4)
Xaa₇-Xaa₈-Glu-Gly-Thr-Phe-Thr-Ser-Asp-Val-Ser-Ser-

Tyr-Leu-Glu-Xaa₂₂-Gln-Ala-Ala-Lys-Glu-Phe-Ile-Ala-

Trp-Leu-Val-Lys-Gly-Arg-R
``` wherein:
Xaa₇ is L-histidine, D-histidine, desamino-histidine, 2amino-histidine, β-hydroxy-histidine, homohistidine, α-fluoromethyl-histidine or α-methyl-histidine;
Xaa₈ is glycine, alanine, valine, leucine, isoleucine, serine or threonine. Preferably, Xaa₈ is glycine, valine, leucine, isoleucine, serine or threonine;
Xaa₂₂ is aspartic acid, glutamic acid, glutamine, asparagine, lysine, arginine, cysteine, or cysteic acid.
R is —NH₂ or Gly(OH).

Another embodiment of the present invention is a glucagon-like peptide-1 (GLP-1) compound having an amino acid other than alanine at position 8 and an amino acid other than glycine at position 22.

Another embodiment of the present invention is a method of stimulating the GLP-1 receptor in a subject in need of GLP-1 receptor stimulation. The method comprises the step of administering to the subject an effective amount of the GLP-1 compounds described herein or the polypeptide having the amino acid sequence of SEQ ID NO: 1, SEQ ID NO: 2, SEQ ID NO:3, SEQ ID NO:4.

Yet another embodiment of the present invention is the GLP-1 compounds described herein or the polypeptide having the amino acid sequence of SEQ ID NO: 1, SEQ ID NO: 2, SEQ ID NO:3, or SEQ ID NO:4 for use in stimulating the GLP-1 receptor in a subject in need of GLP-1. receptor stimulation.

The GLP-1 compounds of the present invention retain GLP-1 receptor activation ability and, in addition, have decreased propensity to aggregate compared with other GLP-1 compounds. As a result, solutions of these compounds can be agitated with minimal conversion to the insoluble, inactive form. This advantage greatly simplifies the manufacturing process. In addition, it is expected that little or no in vivo aggregation will occur after administration to patients, thereby increasing activity and minimizing the potential for adverse reactions. In addition, these GLP-1 compounds are resistant to diaminopeptidase IV degradation and bind zinc and are therefore believed to provide extended time action in vivo.

FIG. 1 shows the amino acid sequences of Val⁸-Glu²²-GLP-1 (7–37)OH (SEQ ID NO: 5), Val⁸-Asp²²-GLP-1 (7–37)OH (SEQ ID NO: 6), Val⁸-Arg²²-GLP-1(7–37)OH (SEQ ID NO: 7) and Val⁸-Lys²²-GLP-1(7–37)OH (SEQ ID NO: 8).

FIG. 2 shows the amino acid sequences of Gly⁸-Glu²²-GLP-1 (7–37)OH (SEQ ID NO: 9), Gly⁸-Asp²²-GLP-1 (7–37)OH (SEQ ID NO: 10), Gly⁸-Arg²²-GLP-1(7–37)OH (SEQ ID NO: 11) and Gly⁸-Lys²²-GLP-1(7–37)OH (SEQ ID NO: 12).

FIG. 3 shows the amino acid sequence of Val⁸-Glu³⁰-GLP-1 (7–37) OH (SEQ ID NO: 13), Gly⁸-Glu³⁰-GLP-1 (7–37)OH (SEQ ID NO: 14), Val⁸-His³⁷-GLP-1(7–37)OH (SEQ ID NO: 15), and Gly⁸-His³⁷-GLP-1(7–37)OH (SEQ ID NO: 16).

FIG. 4 shows the amino acid sequence of Val⁸-Glu²²-Ala²⁷-GLP-1(7–37)OH (SEQ ID NO: 17) and Val⁸-Lys²²-Glu²³-GLP-1 (7–37)OH (SEQ ID NO: 18).

A GLP-1 compound is a polypeptide having from about twenty-five to about thirty-nine naturally occurring or non-naturally occurring amino acids and has sufficient homology to GLP-1(7–37) OH such that it exhibits insulinotropic activity. Examples of non-naturally occurring amino acids include α-methyl amino acids (e.g., α-methyl alanine), D-amino acids, histidine-like amino acids (e.g., 2-amino-histidine, β-hydroxy-histidine, homohistidine, α-fluoromethyl-histidine and α-methyl-histidine), amino acids having an extra methylene in the side chain ("homo" amino acids) and amino acids in which a carboxylic acid functional group in the side chain is replaced with a sulfonic acid group (e.g., cysteic acid). Preferably, however, the GLP-1 compounds of the present invention comprise only naturally occurring amino acids except as otherwise specifically provided herein.

A GLP-1 compound typically comprises a polypeptide having the amino acid sequence of GLP-1(7–37)OH, an analog of GLP-1(7–37)OH, a fragment of GLP-1(7–37)OH or a fragment of a GLP-1(7–37)OH analog. GLP-1(7–37) OH has the amino acid sequence of SEQ ID NO: 19:

```
                                                    (SEQ ID NO: 19)
⁷His-Ala-Glu-¹⁰Gly-Thr-Phe-Thr-Ser-¹⁵Asp-Val-Ser-

Ser-Tyr-²⁰Leu-Glu-Gly-Gln-Ala-²⁵Ala-Lys-Glu-Phe-

Ile-³⁰Ala-Trp-Leu-Val-Lys-³⁵Gly-Arg-³⁷-Gly
```

By custom in the art, the amino terminus of GLP-1(7–37) OH has been assigned number residue 7 and the carboxy-terminus, number 37. The other amino acids in the polypeptide are numbered consecutively, as shown in SEQ ID NO: 19. For example, position 12 is phenylalanine and position 22 is glycine. When not specified, the C-terminal is in the traditional carboxyl form.

A "GLP-1 fragment" is a polypeptide obtained after truncation of one or more amino acids from the N-terminus and/or C-terminus of GLP-1(7–37)OH or a GLP-1(7–37) OH analog. The nomenclature used to describe GLP-1 (7–37)OH carries over to GLP-1 fragments. For example, GLP-1(9–36)OH denotes a GLP-1 fragment obtained by truncating two amino acids from the N-terminus and one amino acid from the C-terminus. The amino acids in the fragment are denoted by the same number as the corresponding amino acid in GLP-1(7–37)OH. For example, the N-terminal glutamic acid in GLP-1(9–36)OH is at position 9; position 12 is occupied by phenylalanine; and position 22 is occupied by glycine, as in GLP-1(7–37)OH.

"GLP-1 compound" also includes polypeptides in which one or more amino acids have been added to the N-terminus and/or C-terminus of GLP-1(7–37)OH or fragments thereof. GLP-1 compounds of this type have up to about thirty-nine amino acids. The amino acids in the "extended" GLP-1 compound are denoted by the same number as the corresponding amino acid in GLP-1(7–37)OH. For example, the N-terminus amino acid of a GLP-1 compound obtained by adding two amino acids to the N-terminal of GLP-1(7–37) OH is at position 5; and the C-terminus amino acid of a GLP-1 compound obtained by adding one amino acids to the C-terminal of GLP-1(7–37)OH is at position 38. Thus, position 12 is occupied by phenylalanine and position 22 is occupied by glycine in both of these "extended" GLP-1 compounds, as in GLP-1(7–37)OH. Amino acids 1–6 of an extended GLP-1 compound are preferably the same as or a conservative substitution of the amino acid at the corresponding position of GLP-1(1–37)OH. Amino acids 38–45 of an extended GLP-1 compound are preferably the same as or a conservative substitution of the amino acid at the corresponding position of glucagon or exendin-4.

A "GLP-1 analog" has sufficient homology to GLP-1(7-37)OH or a fragment of GLP-1(7–37)OH such that the analog has insulinotropic activity. Preferably, a GLP-1 analog has the amino acid sequence of GLP-1(7–37)OH or a fragment thereof, modified so that from one, two, three, four or five amino acids differ from the amino acid in corresponding position of GLP-1(7–37)OH or the fragment of GLP-1(7–37)OH. In the nonmenclature used herein to designate GLP-1 compounds, the substituting amino acid and its position is indicated prior to the parent structure. For example, Glu$^{22}$-GLP-1(7–37)OH designates a GLP-1 compound in which the glycine normally found at position 22 of GLP-1(7–37)OH has been replaced with glutamic acid; Val8-Glu$^{22}$-GLP-1(7–37)OH designates a GLP-1 compound in which alanine normally found at position 8 and glycine normally found at position 22 of GLP-1(7–37)OH have been replaced with valine and glutamic acid, respectively.

The N-terminus of a GLP-1 compound is generally unsubstituted but can also be alkylated or acylated (preferably C1–C20). The C-terminus can be unsubstituted, as is the case with GLP-1(7–37)OH, amidated with —NH$_2$, —NHR or NRR' or esterified with —OR". R and R' are independently alkyl or acyl groups (preferably C1–C20). R" is an alkyl (C1–C20). GLP-1(7–36)NH$_2$ is an example of an "amidated GLP compound". Preferably, the GLP-1 compounds of the present invention have a C-terminus that is unsubstituted or substituted with —NH$_2$.

Preferably GLP-1 compounds of the present invention comprise GLP-1 analogs or fragments of GLP-1 analogs wherein the backbone for such analogs or fragments contains an amino acid other than alanine at position 8 (position 8 analogs). The backbone may also include L-histidine, D-histidine, or modified forms of histidine such as desamino-histidine, 2-amino-histidine, β-hydroxy-histidine, homohistidine, α-fluoromethyl-histidine, or α-methyl-histidine at position 7. It is preferable that these position 8 analogs contain one or more additional changes at positions 11, 12, 16, 22, 23, 24, 26, 27, 30, 33, 34, 35, 36, and 37 compared to the corresponding amino acid of native GLP-1(7–37)OH. It is more preferable that these position 8 analogs contain one or more additional changes at positions 12, 16, 22, 23, 26, 30, 35, and 37 compared to the corresponding amino acid of native GLP-1(7–37)OH. It is even more preferable that these position 8 analogs contain one or more additional changes at positions 22, 23, 27, 30, and 37 compared to the corresponding amino acid of native GLP-1(7–37)OH.

It is also preferable that these analogs have 6 or fewer changes compared to the corresponding amino acids in native GLP-1(7–37)OH. More preferred analogs have 5 or fewer changes compared to the corresponding amino acids in native GLP-1(7–37)OH or have 4 or fewer changes compared to the corresponding amino acids in native GLP-1(7–37)OH. It is even more preferable that these analogs have 3 or fewer changes compared to the corresponding amino acids in native GLP-1(7–37)OH. It is most preferable that these analogs have 2 or fewer changes compared to the corresponding amino acids in native GLP-1(7–37)OH.

It has been found that these substitutions reduce the propensity of GLP-1 compounds to aggregate and generate the insoluble form. The GLP-1 compounds of the present invention generally aggregate at least about 5 times less rapidly than GLP-1(7–37)OH when assessed, for example, by the aggregation assay described in Example 3, preferably at least 20 times less rapidly, more preferably at least 40 times less rapidly, more preferably at least about 50 times less rapidly, even more preferably about 60 times less rapidly, and even more preferably at least about 65 times less rapidly. Preferably, GLP-1 compounds described herein are analogs of GLP-1(7–36)NH$_2$ or GLP-1(7–37)OH.

In a preferred embodiment, the amino acid at position 22 of the GLP-1 compound of the present invention has a side chain which comprises at least two carbon atoms and a polar or charged functional group. Aspartic acid, which has a methylene and carboxyl carbon, is included. More preferably, the side chain of the amino acid at position 22 is a straight or branched chain alkyl group with from two to six carbon atoms and a charged functional group, e.g., a carboxylic acid, an amine, guanidino group or a sulfonic acid group. Thus, examples of preferred amino acids at position 22 include glutamic acid, aspartic acid, arginine and lysine. When position 22 is aspartic acid, glutamic acid, arginine or lysine, position 8 is preferably glycine, valine, leucine, isolecine, serine, threonine or methionine and more preferably valine or glycine. An example of an amino acid with a sulfonic acid group in the side chain cysteic acid (—NH—CH(CH$_2$SO$_3$)—CO—, abbreviated as "Cya"). When position 22 is a sulfonic acid such as cysteic acid, position 8 is preferably glycine, valine, leucine, isolecine, serine, threonine or methionine and more preferably valine or glycine.

In another preferred embodiment, the amino acid at position 8 is preferably glycine, valine, leucine, isoleucine, serine, threonine, or methionine and more preferably valine or glycine and position 30 is glutamic acid, aspartic acid, serine, or histidine and more preferably glutamic acid.

In another preferred embodiment, the amino acid at position 8 is preferably glycine, valine, leucine, isoleucine, serine, threonine, or methionine and more preferably valine or glycine and position 37 is histidine, lysine, arginine, threonine, serine, glutamic acid, aspartic acid, tryptophan, tyrosine, phenylalanine and more preferably histidine.

In another preferred embodiment, the amino acid at position 8 is preferably glycine, valine, leucine, isoleucine, serine, threonine, or methionine and more preferably valine or glycine and position 22 is glutamic acid, lysine, aspartic acid, or arginine and more preferably glutamine acid or lysine and position 23 is lysine, arginine, glutamic acid, aspartic acid, and histidine and more preferably lysine or glutamic acid.

In another preferred embodiment, the amino acid at position 8 is preferably glycine, valine, leucine, isoleucine, serine, threonine, or methionine and more preferably valine or glycine and position 22 is glutamic acid, lysine, aspartic acid, or arginine and more preferably glutamine acid or lysine and position 27 is alanine, lysine, arginine, tryptophan, tyrosine, phenylalanine, or histidine and more preferably alanine.

In another preferred embodiment, the GLP-1 compounds of the present invention have an amino acid at position 8 and have one, two, or three amino acids selected from the group consisting of position 11, position 12, position 16, position 22, position 23, position 24, position 26, position 27, position 30, position 33, position 34, position 35, position 36, and position 37, which differ from the amino acid at the corresponding position of native GLP-1(7–37)OH.

In another preferred embodiment, the GLP-1 compounds of the present invention have one or two amino acids, in addition to the amino acid at position 8, selected from the group consisting of position 11, position 12, position 16, position 22, position 23, position 24, position 26, position 27, position 30, position 33, position 34, position 35, position 36, and position 37, which differ from the amino acid at the corresponding position of native GLP-1(7–37)OH.

As described above, the GLP-1 compounds of the present invention can have amino acids in addition to those at position 8, 11, 12, 16, 22, 23, 24, 26, 27, 30, 33, 34, 35, 36, and 37 which differ from the amino acid at the corresponding position of GLP-1(7–37) or a fragment of GLP-1(7–37). The amino acids other than those at positions 8, 11, 12, 16, 22, 23, 24, 26, 27, 30, 33, 34, 35, 36, and 37 in the GLP compound which differ from the amino acid in corresponding position of GLP-1(7–37)OH are preferably conservative substitutions and, more preferably, are highly conservative substitutions.

Preferably, the GLP-1 compounds of the present invention have zero, one, two or three amino acids in addition to the amino acids at positions 8 and 22 which differ from the amino acid at the corresponding position of GLP-1(7–37) OH or a GLP-1(7–37)OH fragment. In one example, one or more of the amino acids at positions 7, 21 and 27 of the GLP-1 compound differ from the corresponding amino acid in GLP-1(7–37)OH or a GLP-1(7–37)OH fragment, in addition to the amino acids at positions 8 and 22.

Preferably, only positions 7, 8 and 22 differ from the amino acid at the corresponding position of GLP-1(7–37) OH (or a fragment thereof). It is expected that other improved GLP-1 compounds with reduced aggregating properties can be obtained from known, biologically active GLP-1 compounds by replacing glycine at position 22 and preferably alanine at position 8-of these compounds with a suitable amino acid, as described herein. Known biologically active GLP-1 compounds are disclosed in U.S. Pat. No 5,977,071 to Hoffmann, et al., U.S. Pat. No. 5,545,618 to Buckley, et al., Adelhorst, et al., *J. Biol. Chem.* 269:6275 (1994), the entire teachings of which are incorporated herein by reference.

A "conservative substitution" is the replacement of an amino acid with another amino acid that has the same net electronic charge and approximately the same size and shape. Amino acids with aliphatic or substituted aliphatic amino acid side chains have approximately the same size when the total number carbon and heteroatoms in their side chains differs by no more than about four. They have approximately the same shape when the number of branches in the their side chains differs by no more than one. Amino acids with phenyl or substituted phenyl groups in their side chains are considered to have about the same size and shape. Listed below are five groups of amino acids. Replacing an amino acid in a GLP-1 compound with another amino acid from the same groups results in a conservative substitution:

Group I: glycine, alanine, valine, leucine, isoleucine, serine, threonine, cysteine, and non-naturally occurring amino acids with C1–C4 aliphatic or C1–C4 hydroxyl substituted aliphatic side chains (straight chained or monobranched).

Group II: glutamic acid, aspartic acid and non-naturally occurring amino acids with carboxylic acid substituted C1–C4 aliphatic side chains (unbranched or one branch point).

Group III: lysine, ornithine, arginine and non-naturally occurring amino acids with amine or guanidino substituted C1–C4 aliphatic side chains (unbranched or one branch point).

Group IV: glutamine, asparagine and non-naturally occurring amino acids with amide substituted C1–C4 aliphatic side chains (unbranched or one branch point).

Group V: phenylalanine, phenylglycine, tyrosine and tryptophan.

Except as otherwise specifically provided herein, conservative substitutions are preferably made with naturally occurring amino acids.

A "highly conservative substitution" is the replacement of an amino acid with another amino acid that has the same functional group in the side chain and nearly the same size and shape. Amino acids with aliphatic or substituted aliphatic amino acid side chains have nearly the same size when the total number carbon and heteroatoms in their side chains differs by no more than two. They have nearly the same shape when they have the same number of branches in the their side chains. Example of highly conservative substitutions include valine for leucine, threonine for serine, aspartic acid for glutamic acid and phenylglycine for phenylalanine. Examples of substitutions which are not highly conservative include alanine for valine, alanine for serine and aspartic acid for serine.

One example of a GLP-1 compound of the present invention is a polypeptide having the amino acid sequence of SEQ ID NO:1. In a preferred example, the GLP-1 compound is GLP-1(7–37)OH except that $Xaa_8$ is Gly or Val, $Xaa_{22}$ is Glu or Lys, and $Xaa_{23}$ is Glu or Lys. In another example, the GLP-1 compound is GLP-1(7–37)OH except that $Xaa_8$ is Gly or Val and $Xaa_{30}$ is Glu. An additional example is a GLP-1 compound which is GLP-1(7–37)OH except that $Xaa_8$ is Gly or Val and $Xaa_{37}$ is His.

Another example of a GLP-1 compound of the present invention is a polypeptide having the amino acid sequence of SEQ ID. No. 4. In a preferred example, $Xaa_7$ is L-histidine, D-histidine, desamino-histidine, 2amino-histidine, β-hydroxy-histidine, homohistidine, α-fluoromethyl-histidine and α-methyl-histidine, $Xaa_8$ is glycine, alanine, valine, leucine, isoleucine, serine, or threonine, and preferably, glycine, valine, leucine, isoleucine, serine, or threonine, R is —$NH_2$ or Gly(OH) and $Xaa_{22}$ is lysine, glutamic acid, aspartic acid or arginine in SEQ ID NO:4. In a more preferred example, $Xaa_7$ is L-histidine, $Xaa_8$ is glycine or valine, $Xaa_{22}$ is lysine, glutamic acid, aspartic acid or arginine and R is Gly (OH). Alternatively, $Xaa_7$, $Xaa_8$ and R in SEQ ID NO: 4 are as described above and $Xaa_{22}$ is an amino acid with a side chain comprising a sulfonic acid group, e.g., cysteic acid.

In another example of GLP-1 compounds of the present invention, the amino acid at position 8 is not a D-amino acid and does not have the side chain of glycine, serine, threonine, cysteine or beta-alanine when the amino acid at position 22 has a C1–C2 alkyl side chain, a C1–C2 hydroxylated alkyl side chain or a C1–C2 thiolated alkyl chain (e.g., cysteine). In a preferred example of GLP-1 compounds of the present invention, the amino acid at position 8 is not a D-amino acid and does not have the side chain of glycine, serine, threonine, cysteine or beta-alanine when the amino acid at position 22 has a C1–C4 alkyl side chain, a C1–C4 hydroxylated alkyl side chain or a C1–C4 thiolated alkyl chain.

In another example of the GLP-1 compounds of the present invention, the amino acid at position 8 is glycine, valine, leucine, isoleucine, methionine, serine, threonine, cysteine, aspartic acid, glutamic acid, lysine, arginine, asparagine, glutamine, phenylalanine, tyrosine, histidine or tryptophan; and the amino acid at position 22 is aspartic acid, glutamic acid, lysine, arginine, asparagine, glutamine or histidine.

Specific examples of GLP-1 compounds of the present invention include $Glu^{22}$-GLP-1(7–37)OH (SEQ ID NO: 20), $Asp^{22}$-GLP-1(7–37)OH (SEQ ID NO: 21), $Arg^{22}$-GLP-1(7–37)OH (SEQ ID NO: 22), $Lys^{22}$-GLP-1(7–37)OH (SEQ ID NO: 23), $Cya^{22}$-GLP-1(7–37)OH (SEQ ID NO: 24), $Val^8$-$Glu^{22}$-GLP-1(7–37)OH (SEQ ID NO: 5), $Val^8$-$Asp^{22}$-GLP-1(7–37)OH (SEQ ID NO: 6), $Val^8$-$Arg^{22}$-GLP-1(7–37)OH (SEQ ID NO: 7), $Val^8$-$Lys^{22}$-GLP-1(7–37)OH (SEQ ID NO: 8), $Val^8$-$Cya^{22}$-GLP-1(7–37)OH (SEQ ID NO: 25), $Gly^8$-$Glu^{22}$-GLP-1(7–37)OH (SEQ ID NO: 9), $Gly^8$-$Asp^{22}$-GLP-1(7–37)OH (SEQ ID NO: 10), $Gly^8$-$Arg^{22}$-GLP-1(7–37)OH (SEQ ID NO: 11), $Gly^8$-$Lys^{22}$-GLP-1(7–37)OH (SEQ ID NO: 12), $Gly^8$-$Cya^{22}$-GLP-1(7–37)OH (SEQ ID NO: 26), $Glu^{22}$-GLP-1(7–36)$NH_2$ (SEQ ID NO: 27), $Asp_{22}$-GLP-1(7–36)$NH_2$ (SEQ ID NO: 28), $Arg_{22}$-GLP-1(7–36)$NH_2$ (SEQ ID NO: 29), $Lys^{22}$-GLP-1(7–36)$NH_2$ (SEQ ID NO: 30), $Cya^{22}$-GLP-1(7–36)$NH_2$ (SEQ ID NO: 31), $Val_8$-$Glu^{22}$-GLP-1(7–36)$NH_2$ (SEQ ID NO: 32), $Val_8$-$Asp^{22}$-GLP-1(7–36)$NH_2$ (SEQ ID NO: 33), $Val_8$-$Arg^{22}$-GLP-1(7–36)$NH_2$ (SEQ ID NO: 34), $Val^8$-$Lys^{22}$-GLP-1(7–36)$NH_2$ (SEQ ID NO: 35), $Val^8$-$Cya^{22}$-GLP-1(7–36)$NH_2$ (SEQ ID NO: 36), $Gly^8$-$Glu^{22}$-GLP-1(7–36)$NH_2$ (SEQ ID NO: 37), $Gly_8$-$Asp^{22}$-GLP-1(7–36)$NH_2$ (SEQ ID NO: 38), $Gly_8$-$Arg^{22}$-GLP-1(7–36)$NH_2$ (SEQ ID NO: 39), $Gly_8$-$Lys^{22}$-GLP-1(7–36)$NH_2$ (SEQ ID NO: 40) and $Gly_8$-$Cya^{22}$-GLP-1(7–36)$NH_2$ (SEQ ID NO: 41), $Val^8$-$Lys^{23}$-GLP-1(7–37)OH (SEQ ID NO: 42), $Val^8$-$Ala^{27}$-GLP-1(7–37)OH (SEQ ID NO: 43), $Val^8$-$Glu^{30}$-GLP-1(7–37)OH (SEQ ID NO: 44), $Gly^8$-$Glu^{30}$-GLP-1(7–37)OH (SEQ ID NO: 45), $Val^8$-$His^{35}$-GLP-1(7–37)OH (SEQ ID NO: 46), $Val^8$-$His^{37}$-GLP-1(7–37)OH (SEQ ID NO: 47), $Val^8$-$Glu^{22}$-$Lys^{23}$-GLP-1(7–37)OH (SEQ ID NO: 48), $Val^8$-$Glu^{22}$-$Glu^{2}$-GLP-1(7–37)OH (SEQ ID NO: 49), $Val^8$-$Glu^{22}$-Ala 27-GLP-1(7–37)OH (SEQ ID NO: 50), $Val^8$-$Gly^{34}$-$Lys^{35}$-GLP-1(7–37)OH (SEQ ID NO: 51), $Val^8$-$His^{37}$-GLP-1(7–37)OH (SEQ ID NO: 52), $Gly^8$-$His^{37}$-GLP-1(7–37)OH (SEQ ID NO: 53).

As used herein, the term "GLP-1 compound" also includes pharmaceutically acceptable salts of the compounds described herein. A GLP-1 compound of this invention can possess a sufficiently acidic, a sufficiently basic, or both functional groups, and accordingly react with any of a number of inorganic bases, and inorganic and organic acids, to form a salt. Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, and the like.

The GLP-1 compounds can be used to treat subjects with a wide variety of diseases and conditions. It is believed that GLP-1 compounds, including those of the present invention, exert their biological effects by acting at a receptor referred to as the "GLP-1 receptor" (see U.S. Pat. No. 5,670,360 to Thorrens). Subjects with diseases and/or conditions that respond favorably to GLP-1 receptor stimulation or to the adminstration of GLP-1 compounds can therefore be treated with the GLP-1 compounds of the present invention. These subjects are said to "be in need of treatment with GLP-1 compounds" or "in need of GLP-1 receptor stimulation". Included are subjects with non-insulin dependent diabetes, insulin dependent diabetes, stroke (see WO 00/16797 by Efendic), myocardial infarction (see WO 98/08531 by Efendic), obesity (see WO 98/19698 by Efendic), catabolic changes after surgery (see U.S. Pat. No. 6,006,753 to Efendic), functional dyspepsia and irritable bowel syndrome (see WO 99/64060 by Efendic). Also included are subjects requiring prophylactic treatment with a GLP-1 compound, e.g., subjects at risk for developing non-insulin dependent diabetes (see WO 00/07617). Subjects with impaired glucose tolerance or impaired fasting glucose, subjects whose body weight is about 25% above normal body weight for the subject's height and body build, subjects with a partial pancreatectomy, subjects having one or more parents with non-insulin dependent diabetes, subjects who have had gestational diabetes and subjects who have had acute or chronic pancreatitis are at risk for developing non-insulin dependent diabetes.

An "effective amount" of a GLP-1 compound is the quantity which results in a desired therapeutic and/or prophylactic effect without causing unacceptable side-effects when administered to a subject in need of GLP-1 receptor stimulation. A "desired therapeutic effect" includes one or more of the following: 1) an amelioration of the symptom(s) associated with the disease or condition; 2) a delay in the onset of symptoms associated with the disease or condition; 3) increased longevity compared with the absence of the treatment; and 4) greater quality of life compared with the absence of the treatment. For example, an "effective amount" of a GLP-1 compound for the treatment of diabetes is the quantity that would result in greater control of blood glucose concentration than in the absence of treatment, thereby resulting in a delay in the onset of diabetic complications such as retinopathy, neuropathy or kidney disease. An "effective amount" of a GLP-1 compound for the prevention of diabetes is the quantity that would delay, compared with the absence of treatment, the onset of elevated blood glucose levels that require treatment with anti-hypoglycaemic drugs such as sulfonyl ureas, thiazolidinediones, insulin and/or bisguanidines.

An "effective amount" of the GLP-1 compound administered to a subject will also depend on the type and severity of the disease and on the characteristics of the subject, such as general health, age, sex, body weight and tolerance to drugs. The skilled artisan will be able to determine appropriate dosages depending on these and other factors. Typically, a therapeutically effective amount of GLP-1 compound can range from about 0.01 mg per day to about 1000 mg per day for an adult. Preferably, the dosage ranges from about 0.1 mg per day to about 100 mg per day, more preferably from about 1.0 mg/day to about 10 mg/day.

The GLP-1 compounds of the present invention can, for example, be administered orally, by nasal administration, inhalation or parenterally. Parenteral administration can include, for example, systemic administration, such as by intramuscular, intravenous, subcutaneous, or intraperitoneal injection. The GLP-1 compounds can be administered to the subject in conjunction with an acceptable pharmaceutical carrier, diluent or excipient as part of a pharmaceutical composition for treating the diseases discussed above. The pharmaceutical composition can be a solution or, if administered parenterally, a suspension of the GLP-1 compound or a suspension of the GLP-1 compound complexed with a divalent metal cation, as described below. Suitable pharmaceutical carriers may contain inert ingredients which do not interact with the peptide or peptide derivative. Standard pharmaceutical formulation techniques may be employed such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Some examples of suitable excipients include lactose, dextrose, sucrose, trehalose, sorbitol, and mannitol.

A "subject" is a mammal, preferably a human, but can also be an animal, e.g., companion animals (e.g., dogs, cats, and the like), farm animals (e.g., cows, sheep, pigs, horses, and the like) and laboratory animals (e.g., rats, mice, guinea pigs, and the like).

The GLP-1 compounds of the present invention can be complexed with a suitable divalent metal cation. Divalent metal complexes of GLP-1 compounds are generally insoluble in aqueous solution around physiological pH. Thus, these complexes can be administered subcutaneously as suspensions and show a decreased rate of release in vivo, thereby extending the time action the compound. Examples of suitable divalent metal cations include $Zn^{++}$, $Mn^{++}$, $Fe^{++}$, $Ca^{++}$, $Co^{++}$, $Cd^{++}$, $Ni^{++}$, and the like. $Zn^{++}$ is preferred.

To obtain the complexes between the GLP-1 compounds of the present invention and a divalent metal cation, a GLP-1 is dissolved in a suitable buffer and in the presence of a metal salt. The mixture is allowed to incubate at ambient temperature to allow the complex to precipitate. Suitable buffers are those which maintain the mixture at a pH range from about 3.0 to about 9.0 and do not interfere with the complexation reaction. Examples include phosphate buffers, acetate buffers, citrate buffers and Goode's buffers, e.g., HEPES, Tris and Tris acetate. Suitable metal salts are those in which the metal is available for complexation. Examples of suitable zinc salts include zinc chloride, zinc acetate, zinc oxide, and zinc sulfate. Preferably, a divalent metal cationic salt such as zinc chloride is provided in excess to provide a molar ratio of up to about 50 molecules of a divalent metal cation for each molecule of GLP-1 compound.

"Insulinotropic activity" refers to stimulating insulin secretion in response to elevated glucose levels, thereby causing glucose uptake by cells and decreased serum glucose levels. Insulinotropic activity can be assessed by methods known in the art, including using in vivo experiments and in vitro assays that measure GLP-1 receptor binding activity or receptor activation, e.g., assays employing pancreatic islet cells or insulinoma cells, as described in EP 619,322 to Gelfand, et al., and U.S. Pat. No. 5,120,712, respectively. The entire teachings of these references are incorporated herein by reference.

The GLP-1 compounds of the present invention can be prepared by using standard methods of solid-phase peptide synthesis techniques. Peptide synthesizers are commercially available from, for example, Applied Biosystems in Foster City Calif. Reagents for solid phase synthesis are commercially available, for example, from Midwest Biotech (Fishers, Ind.). Solid phase peptide synthesizers can be used according to manufacturers instructions for blocking interfering groups, protecting the amino acid to be reacted, coupling, decoupling, and capping of unreacted amino acids.

Typically, an α-N-carbamoyl protected amino acid and the N-terminal amino acid on the growing peptide chain on a resin is coupled at room temperature in an inert solvent such as dimethylformamide, N-methylpyrrolidone or methylene chloride in the presence of coupling agents such as dicyclohexylcarbodiimide and 1-hydroxybenzotriazole and a base such as diisopropylethylamine. The α-N-carbamoyl protecting group is removed from the resulting peptide resin using a reagent such as trifluoroacetic acid or piperidine, and the coupling reaction repeated with the next desired N-protected amino acid to be added to the peptide chain. Suitable amine protecting groups are well known in the art and are described, for example, in Green and Wuts, "*Protecting Groups in Organic Synthesis*", John Wiley and Sons, 1991, the entire teachings of which are incorporated by reference. Examples include t-butyloxycarbonyl (tBoc) and fluorenylmethoxycarbonyl (Fmoc).

The peptides are also synthesized using standard automated solid-phase synthesis protocols using t-butoxycarbonyl- or fluorenylmethoxycarbonyl-alpha-amino acids with appropriate side-chain protection. After completion of synthesis, peptides are cleaved from the solid-phase support with simultaneous side-chain deprotection using standard hydrogen fluoride methods. Crude peptides are then further purified using Reversed-Phase Chromatography on Vydac C18 columns using acetonitrile gradients in 0.1% trifluoroacetic acid (TFA). To remove acetonitrile, peptides are lyophilized from a solution containing 0.1% TFA, acetonitrile and water. Purity can be verified by analytical reversed phase chromatography. Identity of peptides can be verified by mass spectrometry. Peptides can be solubilized in aqueous buffers at neutral pH.

The invention is illustrated by the following examples which are not intended to be limiting in any way.

EXAMPLE 1

Preparation of the GLP-1 Compounds of the Present Invention by Solid Phase t-Boc Chemistry Approximately 0.5–0.6 grams (0.38–0.45 mmole) Boc Gly-PAM resin was placed in a standard 60 ml reaction vessel and double couplings were run on an Applied Biosytems ABI430A peptide synthesizer. The following side-chain protected amino acids (2 mmole cartridges of Boc amino acids) were obtained from Midwest Biotech (Fishers, Ind.) and used in the synthesis:

Arg-Tosyl (TOS), Asp-δ-cyclohexyl ester(CHXL), Glu-δ-cycohexyl ester (CHXL), His-benzyloxymethyl(BOM), Lys-2-chlorobenzyloxycarbonyl (2Cl-Z), Met-sulfoxide (O), Ser-O-benzyl ether (OBzl), Thr-O-benzyl ether (OBzl), Trp-formyl (CHO) and Tyr-2-bromobenzyloxycarbonyl (2Br-Z) and Boc Gly PAM resin. Trifluoroacetic acid (TFA), di-isopropylethylamine (DIEA), 0.5 M hydroxybenzotriazole (HOBt) in DMF and 0.5 M dicyclohexylcarbodiimide (DCC) in dichloromethane were purchased from PE-Applied Biosystems (Foster City, Calif.). Dimethylformamide (DMF-Burdick and Jackson) and dichloromethane (DCM-Mallinkrodt) were purchased from Mays Chemical Co. (Indianapolis, Ind.).

Standard double couplings were run using either symmetric anhydride or HOBt esters, both formed using DCC. A second set of double couplings (without TFA deprotection) were run at Trp31, Thr13 and Thr11. At the completion of the syntheses, the N-terminal Boc group was removed and the peptidyl resins treated with 20% piperidine in DMF to deformylate the Trp side chain. After washing with DCM, the resins were transferred to a TEFLON reaction vessel and dried in vacuo.

For analogs containing Met, an on-the-resin reduction was done using TFA/10% dimethyl sulfide (DMS)/2% concentrated HCl. Cleavages were done by attaching the reaction vessels to a HF (hydrofluoric acid) apparatus (Penninsula Laboratories). 1 ml m-cresol per gram/resin was added and 10 ml HF (purchased from AGA, Indianapolis, Ind.) was condensed into the pre-cooled vessel. 1 ml DMS per gram resin was added when methionine was present. The reactions were stirred one hour in an ice bath and the HF removed in vacuo. The residues were suspended in ethyl ether and the solids were filtered and washed with ether. Each peptide was extracted into aqueous acetic acid and either freeze dried or loaded directly onto a reverse-phase column.

Purifications were run on a 2.2×25cm VYDAC C18 column in buffer A (0.1% Trifluoroacteic acid in water, B: 0.1% TFA in acetonitrile). A gradient of 20% to 90% B was run on an HPLC (Waters) over 120 minutes at 10 ml/minute while monitoring the UV at 280 nm (4.0 A) and collecting one minute fractions. Appropriate fractions were combined, frozen and lyophilized. Dried products were analyzed by HPLC (0.46×15 cm METASIL AQ C18) and MALDI mass spectrometry.

EXAMPLE 2

Preparation of the GLP-1 Compounds of the Present Invention by Solid Phase F-Moc Chemistry Approximately 114 mg (50 mMole) FMOC Gly WANG resin (purchased from NovaBiochem, LaJolla, Calif.) was placed in each programmed well of the 96 well reaction block and double couplings were run on an Advanced ChemTech 396 peptide synthesizer. Analogs with a C-terminal amide were prepared using 75 mg (50 μmole) Rink Amide AM resin (NovaBiochem, LaJolla, Calif.).

The following FMOC amino acids were purchased from Advanced ChemTech (Louisville, Ky.), NovaBiochem (La Jolla, Calif.), and Midwest BioTech (Fishers, Ind.): Arg-2,2,4,6,7-pentamethyldihydrobenzofuran-5-sulfonyl (Pbf), Asn-trityl (Trt), Asp-β-t-Butyl ester (tBu), Glu-δ-t-butyl ester (tBu), Gln-trityl (Trt), His-trityl (Trt), Lys-t-butyloxycarbonyl (Boc), Ser-t-butyl ether (OtBu), Thr-t-butyl ether (OtBu), Trp-t-butyloxycarbonyl (Boc), Tyr-t-butyl ether (OtBu).

Solvents dimethylformamide (DMF-Burdick and Jackson), N-methyl pyrrolidone (NMP-Burdick and Jackson), dichloromethane (DCM-Mallinkrodt) were purchased from Mays Chemical Co. (Indianapolis, Ind.).

Hydroxybenzotrizole (HOBt), di-isopropylcarbodiimde (DIC), di-isopropylethylamine (DIEA), and piperidine (Pip) were purchased from Aldrich Chemical Co (Milwaukee, Wis.).

All amino acids were dissolved in 0.45 M HOBt in NMP and 50 minutes DIC/HOBt activated couplings were run after 20 minutes deprotection using 20% Pip/DMF. Each resin was washed with DMF after deprotections and couplings. After the last coupling and deprotection, the peptidyl resins were washed with DCM and dried in vacuo in the reaction block.

With the reaction/cleavage block assembly in place, 2 ml Reagent K was added to each well and the cleavage reaction mixed for 2 hours [Reagent K=0.75 gm phenol, 0.5 ml thioanisole, 0.25 ml ethanedithiol, 0.5 ml water per 10 ml trifluoroacetic acid (TFA), all purchased from Aldrich Chemical Co., Milwaukee, Wis.]. The TFA filtrates were added to 40 ml ethyl ether and the precipitants centrifuged 2 minutes at 2000 rpm. The supernatants were decanted, the pellets re-suspended in 40 ml ether, re-centrifuged, re-decanted, dried under nitrogen and then in vacuo.

0.3–0.6 mg of each product was dissolved in 1 ml 0.1% TFA/acetonitrile(ACN) and 20 ul was analyzed on HPLC (0.46×15 cm METASIL AQ C18, 1 ml/min, 45° C., 214 nM (0.2 A), A=0.1% TFA, B=0.1% TFA/50% ACN. Gradient=50% B to 90% B over 30 minutes].

Purifications were run on a 2.2×25 cm VYDAC C18 column in buffer A (0.1% trifluoroacteic acid in water, B: 0.1% TFA in acetonitrile). A gradient of 20% to 90% B was run on an HPLC (Waters) over 120 minutes at 10 ml/minute while monitoring the UV at 280 nm (4.0 A) and collecting 1 minute fractions. Appropriate fractions were combined, frozen and lyophilized. Dried products were analyzed by HPLC (0.46×15 cm METASIL AQ C18) and MALDI mass spectrometry.

EXAMPLE 3

GLP Aggregation Assay

GLP peptides of this invention were analyzed with respect to their potential to aggregate in solution. In general, peptides in solution were stirred at elevated temperature in a suitable buffer while recording turbidity at 350 nm as a function of time. Time to the onset of aggregation was measured to quantify the potential of a given GLP molecule to aggregate under these stressed conditions.

Protocol:

A GLP-1 compound was first dissolved under alkaline conditions (pH 10.5) for 30 minutes to dissolve any pre-aggregated material. The solution was then adjusted to pH 7.4 and filtered. Specifically, 4 mg of a lyophilized GLP-1 compound was dissolved in 3 ml of 10 mM phosphate/10 mM citrate. The pH was adjusted to 10.0–10.5 and held for 30 minutes. The solution was adjusted with HCl to pH 7.4 and filtered through a suitable filter, for example a Millex GV syringe filter (Millipore Corporation, Bedford, Mass.). This solution was then diluted to a final sample containing 0.3 mg/mL protein in 10 mM citrate, 10 mM phosphate, 150 mM NaCl, and adjusted to pH 7.4 to 7.5. The sample was incubated at 37° C. in a quartz cuvette. Every five minutes the turbidity of the solution was measured at 350 nm on an AVIV Model 14DS UV-VIS spectrophotometer (Lakewood, N.J.). For 30 seconds prior to and during the measurement the solution was stirred using a magnetic stir bar from Starna Cells, Inc. (Atascadero, Calif.). An increase in OD at 350 nm indicates aggregation of the GLP-peptide. The time to aggregation was approximated by the intersection of linear fits to the pre-growth and growth phase according to method of Drake (Arvinte T, Cudd A, and Drake A F. (1993) *J. Bio. Chem.* 268, 6415–6422).

The cuvette was cleaned between experiments with a caustic soap solution (e.g., Contrad-70).

The results for a number of GLP-1 compounds of the present invention are reported in Table 1 as the time in hours required for the compound to aggregate. As can be seen, the compounds of the present invention show greatly increased aggregation times over GLP-1 compounds known in the prior art.

EXAMPLE 4

GLP-1 Receptor Activation With the GLP-1 Compounds of the Present Invention

The ability of the GLP-1 compounds of the present invention to activate the GLP-1 receptor was assessed using in vitro assays such as those described in EP 619,322 to Gelfand, et al., and U.S. Pat. No. 5,120,712, respectively. The entire teachings of these references are incorporated herein by reference. The activity of these compounds relative to the activity of GLP-1(7–37)OH is reported in Table 1. As can be seen from these results, the activity of the GLP-1 compounds of the present invention is generally about as good as or better than GLP-1(7–37)OH.

TABLE 1

| GLP-1 Compound | Aggregation Time in Hours | GLP-1 Receptor Activation |
|---|---|---|
| GLP-1 (7–37)OH | 1 | 1.0 |
| Val$^8$-GLP-1(7–37)OH | 0.9 ± 0.2 (n = 6) | 0.47 |
| Gly$^8$-His$^{11}$-GLP-1(7–37)OH | 9* | 0.282 |
| Val$^8$-Ala$^{11}$-GLP-1(7–37)OH | 10 | 0.021 |
| Val$^8$-Lys$^{11}$-GLP-1(7–37)OH | 13 | 0.001 |
| Val$^8$-Tyr$^{12}$-GLP-1(7–37)OH | 6 | 0.81 |
| Val$^8$-Glu$^{16}$-GLP-1(7–37)OH | 12 | 0.047 |
| Val$^8$-Ala$^{16}$-GLP-1(7–37)OH | 16 | 0.112 |

TABLE 1-continued

| GLP-1 Compound | Aggregation Time in Hours | GLP-1 Receptor Activation |
|---|---|---|
| Val$^8$-Tyr$^{16}$-GLP-1(7–37)OH | 5 | 1.175 |
| Val$^8$-Lys$^{20}$-GLP-1(7–37)OH | 5 | 0.33 |
| Gln$^{22}$-GLP-1(7–37)OH | 7 | 0.42 |
| Val$^8$-Ala$^{22}$-GLP-1(7–37)OH | 19 | 0.56 |
| Val$^8$-Ser$^{22}$-GLP-1(7–37)OH | 22 | 0.50 |
| Val$^8$-Asp$^{22}$-GLP-1(7–37)OH | >90 | 0.40 |
| Val$^8$-Glu$^{22}$-GLP-1(7–37)OH | 72 | 1.29 |
| Val$^8$-Lys$^{22}$-GLP-1(7–37)OH | 100, 54 | 0.58 |
| Val$^8$-Pro$^{22}$-GLP-1(7–37)OH | >75 | 0.01 |
| Val$^8$-His$^{22}$-GLP-1(7–37)OH | >75 | 0.14 |
| Val$^8$-Lys$^{22}$-GLP-1(7–36)NH$_2$ | 24 | 0.53 |
| Val$^8$-Glu$^{22}$-GLP-1(7–36)NH$_2$ | >65 | 1.0 |
| Gly$^8$-Glu$^{22}$-GLP-1(7–37)OH | 19 | 1.07 |
| Val$^8$-Glu$^{23}$-GLP-1(7–36)OH | 65 | 0.28 |
| Val$^8$-Lys$^{23}$-GLP-1(7–37)OH | >45 | 0.18 |
| Val$^8$-His$^{24}$-GLP-1(7–37)OH | 3 | 0.007 |
| Val$^8$-Lys$^{24}$-GLP-1(7–37)OH | 22 | 0.02 |
| Ala$^8$-His$^{26}$-GLP-1(7–37)OH | >24 | 0.8 |
| Ala$^8$-Glu$^{26}$-GLP-1(7–37)OH | >24 | 0.7 |
| Val$^8$-His$^{27}$-GLP-1(7–37)OH | 10 | 0.37 |
| Val$^8$-Ala$^{27}$-GLP-1(7–37)OH | 2 | 0.47 |
| Gly$^8$-Glu$^{30}$-GLP-1(7–37)OH | >40 | 0.29 |
| Val$^8$-Glu$^{30}$-GLP-1(7–37)OH | 30 | 0.29 |
| Val$^8$-Asp$^{30}$-GLP-1(7–37)OH | >45 | 0.15 |
| Val$^8$-Ser$^{30}$-GLP-1(7–37)OH | 8 | 0.19 |
| Val$^8$-His$^{30}$-GLP-1(7–37)OH | 13 | 0.19 |
| Val$^8$-Glu$^{33}$-GLP-1(7–37)OH | >70 | 0.039 |
| Val$^8$-Ala$^{33}$-GLP-1(7–37)OH | 20 | 0.1 |
| Val$^8$-Gly$^{33}$-GLP-1(7–37)OH | 9 | 0.01 |
| Val$^8$-Glu$^{34}$-GLP-1(7–37)OH | >40* | 0.17 |
| Val$^8$-Pro$^{35}$-GLP-1(7–37)OH | 14 | 0.094 |
| Val$^8$-His$^{35}$-GLP-1(7–37)OH | >45, 30 | 0.41 |
| Val$^8$-Glu$^{35}$-GLP-1(7–37)OH | 63 | 0.15 |
| Val$^8$-Glu$^{36}$-GLP-1(7–37)OH | >45 | 0.11 |
| Val$^8$-His$^{36}$-GLP-1(7–37)OH | 8 | 0.22 |
| Val$^8$-His$^{37}$-GLP-1(7–37)OH | >40 | 0.33 |
| Val$^8$-Leu$^{16}$-Glu$^{26}$-GLP-1(7–37)OH | >20 | 0.23 |
| Val$^8$-Lys$^{22}$-Glu$^{30}$-GLP-1(7–37)OH | 4 | 0.37 |
| Val$^8$-Lys$^{22}$-Glu$^{23}$-GLP-1(7–37)OH | >30 | 0.35 |
| Val$^8$-Glu$^{22}$-Gln$^{23}$-GLP-1(7–37)OH | >20 | 0.47 |
| Val$^8$-Glu$^{22}$-Ala$^{27}$-GLP-1(7–37)OH | >45 | 1.02 |
| Val$^8$-Glu$^{22}$-Lys$^{23}$-GLP-1(7–37)OH | >65 | 1.43 |
| Val$^8$-Lys$^{33}$-Val$^{34}$-GLP-1(7–37)OH | 22 | 0.08 |
| Val$^8$-Lys$^{33}$-Asn$^{34}$-GLP-1(7–37)OH | >48 | 0.09 |
| Val$^8$-Gly$^{34}$-Lys$^{35}$-GLP-1(7–37)OH | 27 | 0.34 |
| Val$^8$-Gly$^{36}$-Pro$^{37}$-GLP-1(7–37)NH$_2$ | 2 | 0.53 |

*Aggregation time determined at 30° C.

EXAMPLE 5

Zinc Precipitation of GLP-1 Compounds

Individual GLP-1 compounds were prepared as described in Examples 1 or 2. 3 mg of an individual lyophilized GLP molecule was dissolved in 3 ml 0.1 M HEPES buffer pH 10.5. The pH of the resulting solution was then adjusted to between 10.0 and 10.5 with 0.2 N NaOH. The solution was stirred at ambient temperature for 30 minutes and the solution was then adjusted to a pH of 7.4 with 0.2 N HCl. The solution was filtered through an appropriate syringe filter, for example a Millex GV syringe filter (Millipore Corporation, Bedford, Mass.), and the concentration of the GLP-1 compound was estimated by measuring the absorption at 280 nm in a spectrophotometer, for example a Beckman DU640. The protein concentration was then adjusted to 200 μM in HEPES pH 7.4.

The filtered GLP-1 solutions (100 μl) were diluted with 100 μl of 0.1 M HEPES pH 7.4 containing various levels of zinc chloride in an ELISA plate, (e.g. Falcon Microtest™ 96) resulting in 200 μl of solution containing various levels of zinc chloride and 100 μM GLP-1 compounds. These solutions were incubated at ambient temperature (22° C.) for hours and then centrifuged, for example, in a Jouan CR412 centrifuge with microplate adapters. 150 μl of the supernatants after centrifugation were then transferred to a UV-readable ELISA microtiter plate (e.g. Costar UV plate) and the OD at 280 was determined in a microplate reader (e.g. Molecular Devices SPECTRAmax PLUS, SOFTmax PRO). The results of an experiment are shown in Table 2. $A_{280}$ values are the result of two independent determinations.

TABLE 2

| Zn/GLP-1 molar ratio | GLP-1 (7–37) OH A280 | Gly⁸ GLP-1 (7–37) OH A280 | Val⁸ GLP-1 (7–37) OH A280 | Gln²² GLP-1 (7–37) OH A280 | Val⁸-Glu²² GLP-1 (7–37) OH A280 | Val⁸-Ala²² GLP-1 (7–37) OH A280 |
|---|---|---|---|---|---|---|
| 0 | 0.337 | 0.32 | 0.3 | 0.290 | 0.295 | 0.289 |
| 0.3 | 0.318 | 0.166 | 0.27 | 0.390 | 0.291 | 0.202 |
| 0.5 | 0.329 | 0.151 | 0.26 | 0.123 | 0.292 | 0.107 |
| 0.7 | 0.253 | 0.156 | 0.124 | 0.076 | 0.293 | 0.104 |
| 1 | 0.148 | 0.119 | 0.06 | 0.074 | 0.26 | 0.110 |
| 2 | 0.092 | 0.089 | 0.025 | 0.095 | 0.078 | 0.110 |
| 3 | 0.081 | 0.085 | 0.021 | 0.095 | 0.052 | 0.104 |
| 5 | 0.074 | 0.078 | 0.019 | 0.097 | 0.035 | 0.119 |

| Zn/GLP-1 molar ratio | Val⁸-Ser²²-GLP-1 (7–37) OH A280 | Val⁸-Phe²²-GLP-1 (7–37) OH A280 | Val⁸-Pro²² GLP-1 (7–37) OH A280 | Val⁸-Lys²² GLP-1 (7–37) OH A280 | Val⁸-Asp²²-GLP-1 (7–37) OH A280 |
|---|---|---|---|---|---|
| 0 | 0.2855 | 0.31 | 0.2595 | 0.299 | 0.288 |
| 0.3 | 0.2805 | 0.1485 | 0.2455 | 0.0825 | 0.2785 |
| 0.5 | 0.2665 | 0.1165 | 0.2325 | 0.0905 | 0.2845 |
| 0.7 | 0.1825 | 0.1015 | 0.219 | 0.1195 | 0.287 |
| 1 | 0.149 | 0.1265 | 0.1905 | 0.1225 | 0.291 |
| 2 | 0.0935 | 0.092 | 0.1695 | 0.1675 | 0.184 |
| 3 | 0.101 | 0.061 | 0.1615 | 0.1475 | 0.1485 |
| 5 | 0.0615 | 0.00795 | 0.171 | 0.142 | 0.1675 |

These results show that only small amounts of zinc are required to complex with and precipitate a significant portion of various GLP-1 compounds from these dilute solutions.

Equivalents

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. An isolated GLP-1 compound comprising the amino acid sequence of formula 1 (SEQ ID NO:1)

(SEQ ID NO: 1)
His-$Xaa_8$-Glu-Gly-$Xaa_{11}$-$Xaa_{12}$-Thr-Ser-Asp-$Xaa_{16}$-Ser-Ser-Tyr-Leu-Glu-$Xaa_{22}$-$Xaa_{23}$-$Xaa_{24}$-Ala-$Xaa_{26}$-$Xaa_{27}$-Phe-Ile-$Xaa_{30}$-Trp-Leu-$Xaa_{33}$-$Xaa_{34}$-$Xaa_{35}$-$Xaa_{36}$-R Formula 1 wherein:
$Xaa_8$ is: Gly, or Val;
$Xaa_{11}$ is: Asp, Glu, Arg, Thr, Ala, Lys, or His;
$Xaa_{12}$ is: His, Trp, Phe, or Tyr;
$Xaa_{16}$ is: Leu, Ser, Thr, Trp, His, Phe, Asp, Val, Tyr, Glu, or Ala;
$Xaa_{22}$ is: Asp, Glu, Gln, Asn, Lys, Arg, Cys, or Cysteic Acid;
$Xaa_{23}$ is: His, Asp, Lys, Glu, Gln, or Arg;
$Xaa_{24}$ is: Glu, Arg, Ala, or Lys;
$Xaa_{26}$ is: Trp, Tyr, Phe, Asp, Lys, Glu, or His;
$Xaa_{27}$ is: Ala, Glu, His, Phe, Tyr, Trp, Arg, or Lys;
$Xaa_{30}$ is: Ala, Glu, Asp, Ser, or His;
$Xaa_{33}$ is: Asp, Arg, Val, Lys, Ala, Gly, or Glu;
$Xaa_{34}$ is: Glu, Lys, or Asp;
$Xaa_{35}$ is: Thr, Ser, Lys, Arg, Trp, Tyr, Phe, Asp, Gly, Pro, His, or Glu;
$Xaa_{36}$ is: Thr, Ser, Asp, Trp, Tyr, Phe, Arg, Glu, or His;
R is: Lys, Arg, Thr, Ser, Glu, Asp, Trp, Tyr, Phe, His, —NH2, Gly, Gly-Pro, or Gly-Pro-NH$_2$, or is deleted, and wherein the GLP-1 compound demonstrates insulinotropic activity.

2. The GLP-1 compound of claim 1 wherein $Xaa_{22}$ is aspartic acid, glutamic acid, lysine, or arginine.

3. The GLP-1 compound of claim 2 wherein $Xaa_{22}$ is glutamic acid.

4. An isolated GLP-1 compound comprising the amino acid sequence of formula II (SEQ ID NO:2):

(SEQ ID NO: 2)
His-Xaa₈-Glu-Gly-Thr-Xaa₁₂-Thr-Ser-Asp-Xaa₁₆-Ser-

Ser-Tyr-Leu-Glu-Xaa₂₂-Xaa₂₃-Ala-Ala-Xaa₂₆-Glu-Phe-

Ile-Xaa₃₀-Trp-Leu-Val-Lys-Xaa₃₅-Arg-R formula II wherein:
- $Xaa_8$ is: Gly, or Val;
- $Xaa_{12}$ is: His, Trp, Phe, or Tyr;
- $Xaa_{16}$ is: Leu, Ser, Thr, Trp, His, Phe, Asp, Val, Glu, or Ala;
- $Xaa_{22}$ is: Asp, Glu, Gln, Asn, Lys, Arg, Cys, or Cysteic Acid;
- $Xaa_{23}$ is: His, Asp, Lys, Glu, or Gln;
- $Xaa_{26}$ is: Asp, Lys, Glu, or His;
- $Xaa_{30}$ is: Ala, Glu, Asp, Ser, or His;
- $Xaa_{35}$ is: Thr, Ser, Lys, Arg, Trp, Tyr, Phe, Asp, Gly, Pro, His, or Glu;
- R is: Lys, Arg, Thr, Ser, Glu, Asp, Trp, Tyr, Phe, His, —NH₂, Gly, Gly-Pro, or Gly-Pro-NH₂, or is deleted, and wherein the GLP-1 compound demonstrates insulinotropic activity.

5. The GLP-1 compound of claim 4 wherein $Xaa_{22}$ is aspartic acid, glutamic acid, lysine, or arginine.

6. The GLP-1 compound of claim 5 wherein $Xaa_{22}$ is glutamic acid.

7. An isolated GLP-1 compound comprising the amino acid sequence of formula III (SEQ ID NO:3):

(SEQ ID NO: 3)
His-Xaa₈-Glu-Gly-Thr-Phe-Thr-Ser-Asp-Val-Ser-Ser-

Tyr-Leu-Glu-Xaa₂₂-Xaa₂₃-Ala-Ala-Lys-Xaa₂₇-Phe-Ile-

Xaa₃₀-Trp-Leu-Val-Lys-Gly-Arg-R formula III wherein:
- $Xaa_8$ is: Gly, or Val;
- $Xaa_{22}$ is: Asp, Glu, Gln, Asn, Lys, Arg, Cys, or Cysteic Acid;
- $Xaa_{23}$ is: His, Asp, Lys, Glu, or Gln;
- $Xaa_{27}$ is: Ala, Glu, His, Phe, Tyr, Trp, Arg, or Lys
- $Xaa_{30}$ is: Ala, Glu, Asp, Ser, or His;
- R is: Lys, Arg, Thr, Ser, Glu, Asp, Trp, Tyr, Phe, His, —NH₂, Gly, Gly-Pro, or Gly-Pro-NH₂, or is deleted, and wherein the GLP-1 compound demonstrates insulinotropic activity.

8. The GLP-1 compound of claim 7 wherein $Xaa_{22}$ is aspartic acid, glutamic acid, lysine, or arginine.

9. The GLP-1 compound of claim 8 wherein $Xaa_{22}$ is glutamic acid.

10. An isolated GLP-1 compound comprising the amino acid sequence of SEQ ID NO: 4:

(SEQ ID NO: 4)
Xaa₇-Xaa₈-Glu-Gly-Thr-Phe-Thr-Ser-Asp-Val-Ser-Ser-

Tyr-Leu-Glu-Xaa₂₂-Gln-Ala-Ala-Lys-Glu-Phe-Ile-Ala-

Trp-Leu-Val-Lys-Gly-Arg-R wherein:
- $Xaa_7$ is L-histidine, D-histidine, desamino-histidine, 2-amino-histidine, β-hydroxy-histidine, homohistidine, α-fluoromethyl-histidine and α-methyl-histidine;
- $Xaa_8$ is glycine or valine;
- $Xaa_{22}$ is aspartic acid, glutamic acid, glutamine, asparagine, lysine, arginine, cysteine, or cysteic acid; and
- R is NH₂ or Gly(OH), and wherein the GLP-1 compound demonstrates insulinotropic activity.

11. The GLP-1 compound of claim 10 wherein $Xaa_{22}$ is lysine, aspartic acid, glutamic acid or arginine.

12. The GLP-1 compound of claim 11 wherein $Xaa_7$ is L-histidine, $Xaa_8$ is glycine or valine and R is Gly(OH).

13. The GLP-1 compound of claim 1, wherein the GLP-1 compound is selected from the group consisting of: Val₈-Glu₂₂-GLP-1(7–37)OH (SEQ ID NO: 5); Val₈-Asp₂₂-GLP-1(7–37)OH (SEQ ID NO: 6); Val₈-Arg₂₂-GLP-1(7–37)OH (SEQ ID NO: 7); and Val₈-Lys₂₂-GLP-1(7–37)OH (SEQ ID NO: 8).

14. The GLP-1 compound of claim 13 wherein the GLP-1 compound is Val$^8$-Glu₂₂-GLP-1(7–37)OH (SEQ ID NO: 5).

* * * * *